(12) United States Patent
Suyama et al.

(10) Patent No.: US 7,550,276 B2
(45) Date of Patent: Jun. 23, 2009

(54) METHOD OF DETECTING NUCLEIC ACID

(75) Inventors: Akira Suyama, Hachioji (JP); Kunio Hori, Chofu (JP)

(73) Assignee: Olympus Corporation, Tokyo (JP)

( * ) Notice: Subject to any disclaimer, the term of this patent is extended or adjusted under 35 U.S.C. 154(b) by 338 days.

(21) Appl. No.: 10/712,715

(22) Filed: Nov. 13, 2003

(65) Prior Publication Data
US 2005/0064441 A1     Mar. 24, 2005

Related U.S. Application Data

(63) Continuation of application No. 09/872,881, filed on Jun. 1, 2001, now abandoned, which is a continuation of application No. PCT/JP00/06919, filed on Oct. 4, 2000.

(30) Foreign Application Priority Data

Oct. 4, 1999   (JP)   ................... 11-283148
Oct. 4, 1999   (JP)   ................... 11-283437

(51) Int. Cl.
   C12P 19/34   (2006.01)
   C12Q 1/68    (2006.01)
   C07H 21/02   (2006.01)
   C07H 21/04   (2006.01)
   C07H 21/00   (2006.01)

(52) U.S. Cl. .................. 435/91.2; 435/6; 435/91.1; 536/23.1; 536/24.3; 536/24.33; 536/25.32

(58) Field of Classification Search .............. 435/6, 435/91.1, 91.2, 183; 436/94; 536/23.1, 24.3, 536/24.33, 25.3
See application file for complete search history.

(56) References Cited

U.S. PATENT DOCUMENTS

| 5,514,543 | A  | 5/1996  | Grossman et al. |
| 5,800,994 | A  | 9/1998  | Martinelli et al. |
| 5,935,793 | A  | 8/1999  | Wong |
| 6,007,987 | A  | 12/1999 | Cantor et al. |
| 6,218,151 | B1 | 4/2001  | Cleuziat et al. |

FOREIGN PATENT DOCUMENTS

| EP | 0 246 864 A2 | 11/1987 |
| EP | 0 466 367 A1 | 1/1992  |
| EP | 0 867 506 A1 | 9/1998  |
| WO | WO 95/11995  | 5/1995  |
| WO | WO 95/27078  | 12/1995 |

(Continued)

OTHER PUBLICATIONS

T.C.H. Hsuih, et al., "Novel, Ligation-Dependent PCR Assay for Detection of Hepatitis C Virus in Serum", *Journal of Clinical Microbiology* 501-507 (1996).

*Primary Examiner*—Frank W Lu
(74) *Attorney, Agent, or Firm*—Scully, Scott, Murphy & Presser, P.C.

(57) ABSTRACT

The present invention relates to a method of detecting or quantifying a target nucleic acid present in a specimen. The present invention provides a method of detecting or quantifying a target nucleic acid by using artificially-designed probes having a flag consisting of a plurality of units, thereby easily and accurately detecting the target nucleic acid.

4 Claims, 14 Drawing Sheets

FOREIGN PATENT DOCUMENTS

| | | |
|---|---|---|
| WO | WO 96/15271 | 5/1996 |
| WO | WO 97/45559 | 12/1997 |
| WO | WO 98/04746 | 2/1998 |
| WO | WO 99/35287 | 7/1999 |
| WO | WO 99/42614 | 8/1999 |

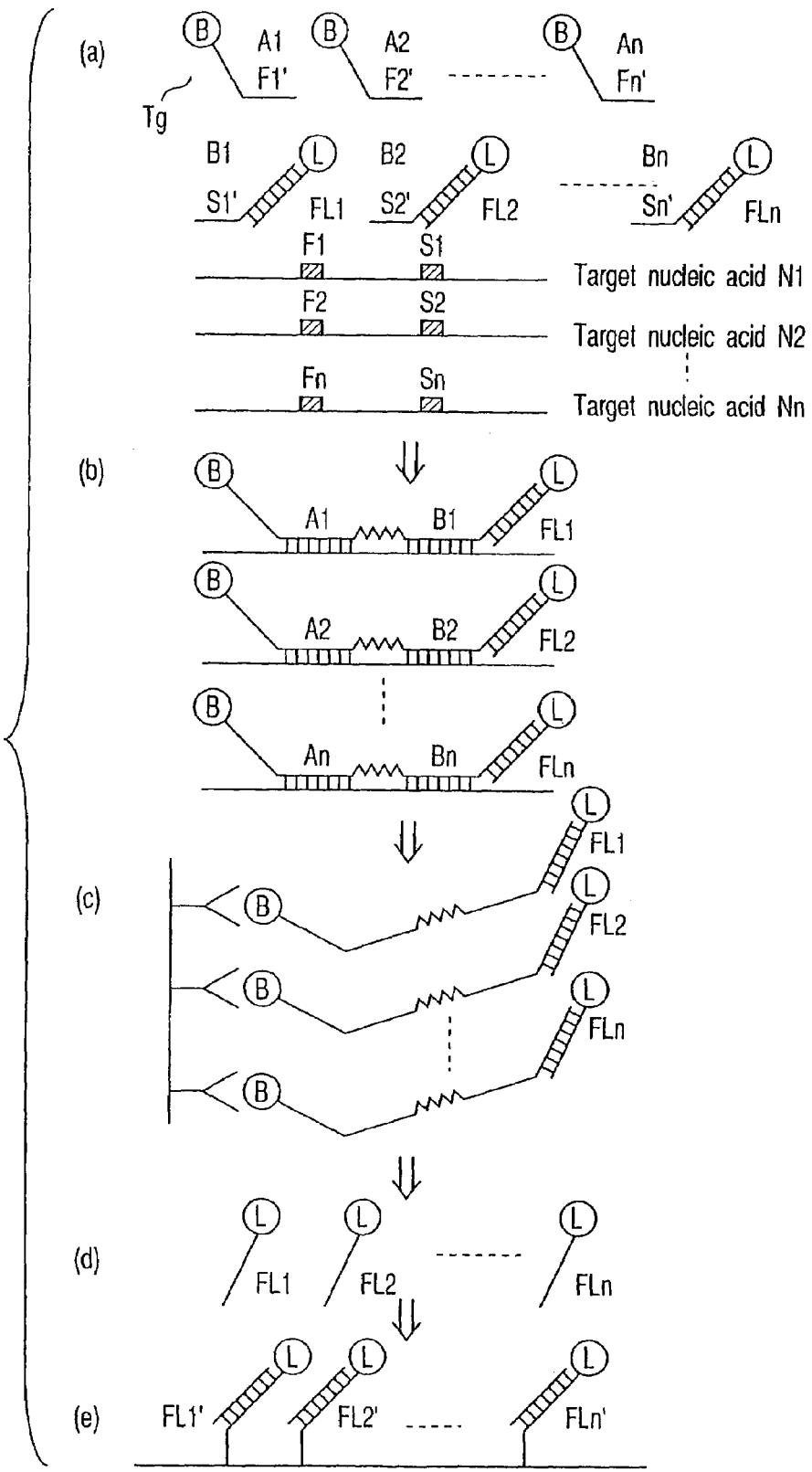
F I G. 2

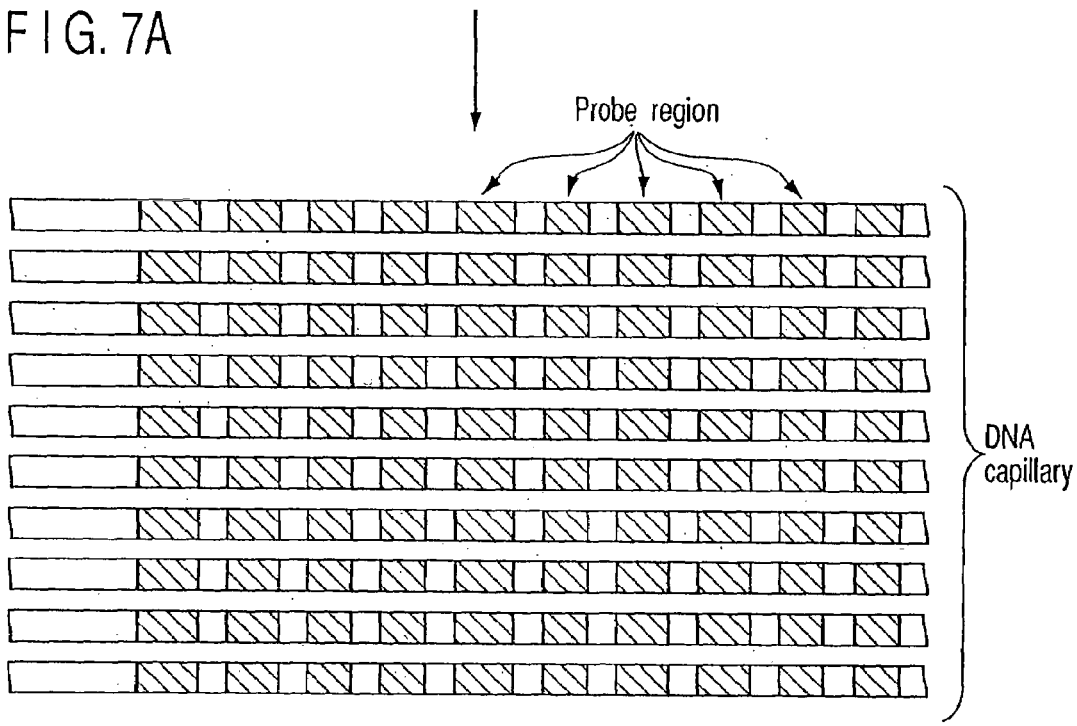
F I G. 7A
F I G. 7B
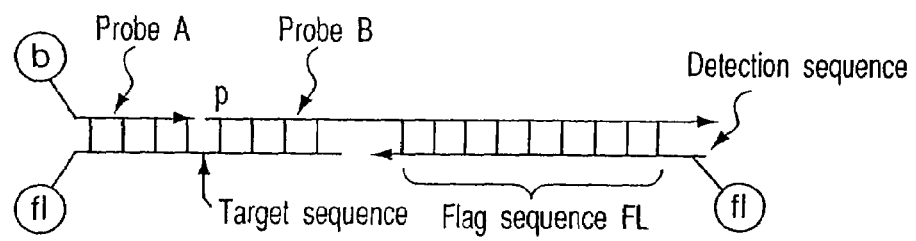
F I G. 8

| Name | Sequence (5'→3') |
|---|---|
| Probe A | b-16A : b-CTAgTAgggTgAAgTC (SEQ ID NO: 1) |
| Probe B | P-16B-48 : P-CATAAgAgCCCTAgAgCATgCTggTCAAggggCACgCggTTCATCAggaAgTCgAAggCAggACg (SEQ ID NO: 2) |
| Target sequence | r-32-fl : CTCTAgggCTCTTATggACTTCACCCTACTAg-fl (SEQ ID NO: 3) |
| Detection sequence | fl-r-48 : fl-CgTCCTgCCTTCgACTCCTgATgAACCgCgTgCCCTTgACCAgCATg (SEQ ID NO: 4) |
| Mutation sequence | fl-neg-r-32AB : fl-TTCTAgAgCTCCTATggACTTCGCCCTACTAg (SEQ ID NO: 5) |

F I G. 9

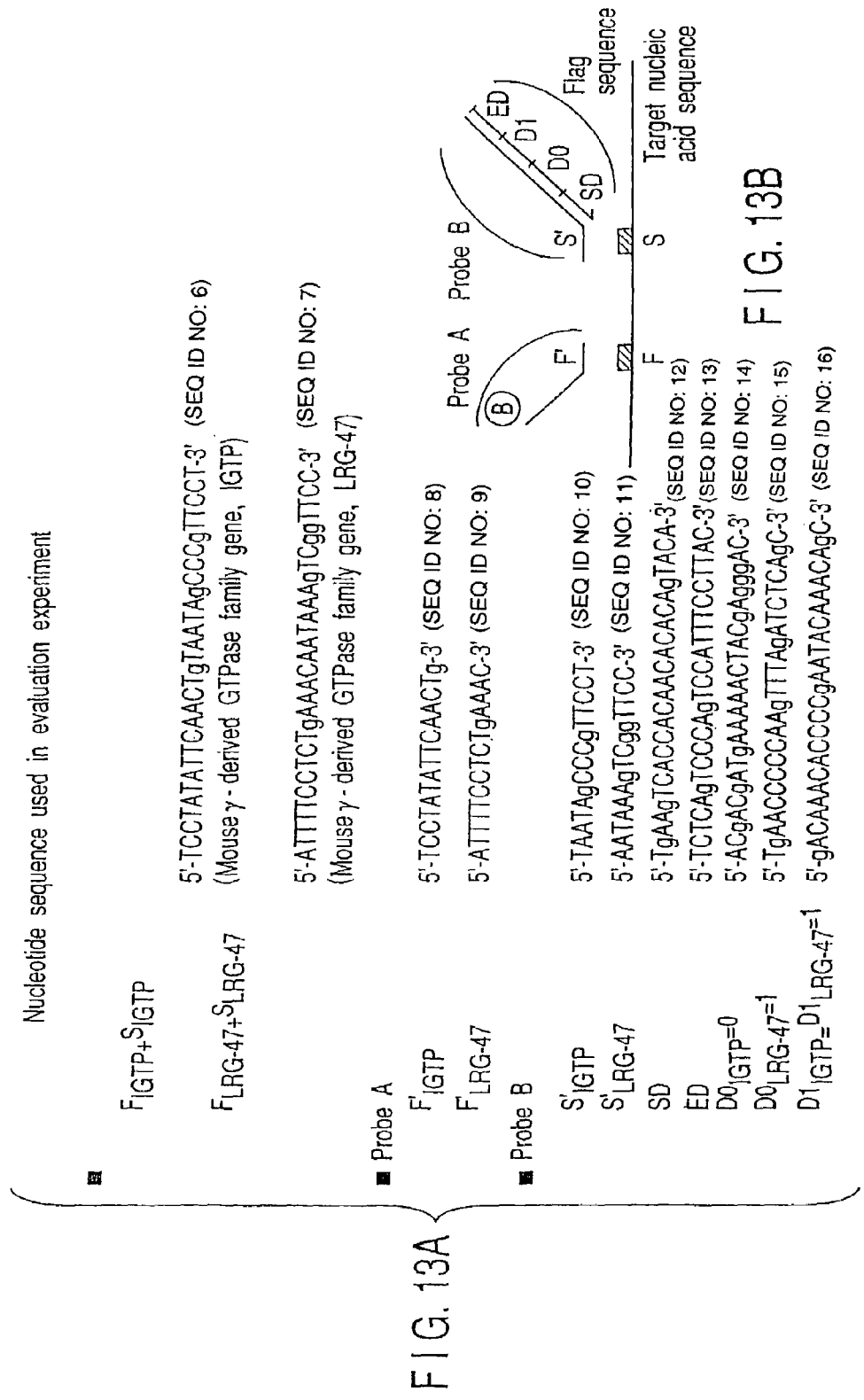

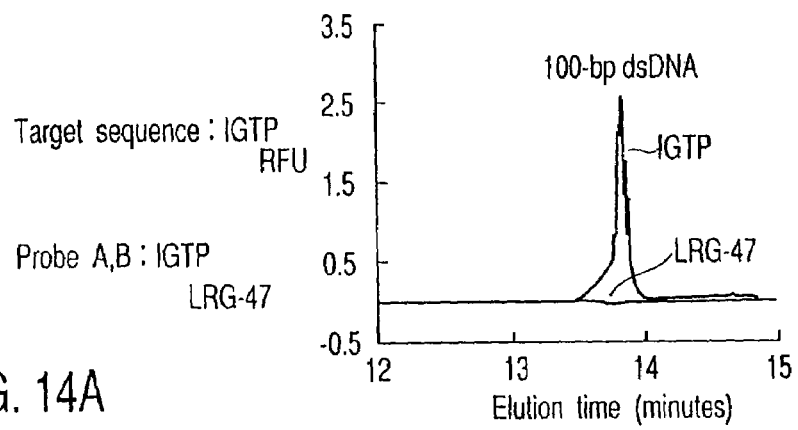
F I G. 14A
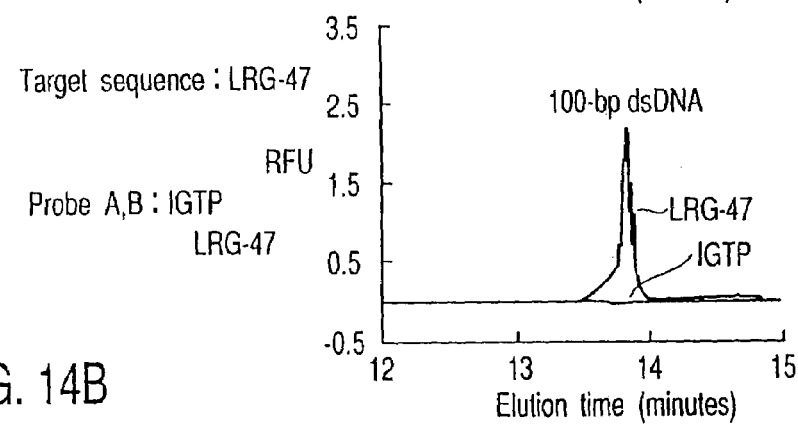
F I G. 14B
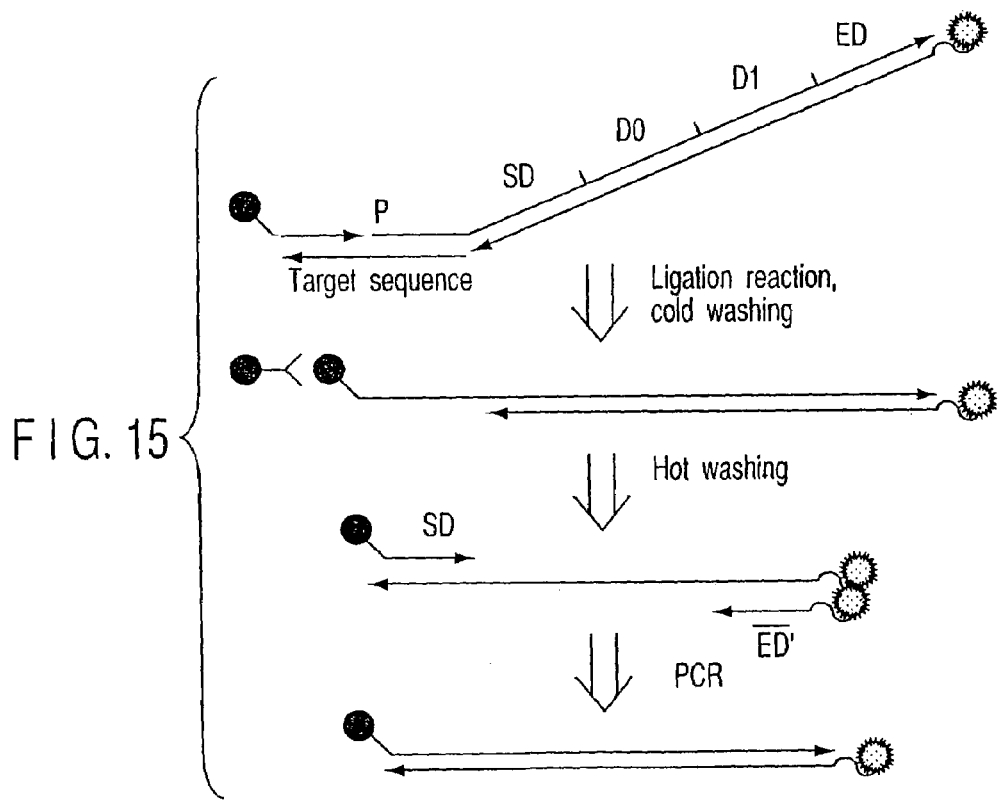
F I G. 15

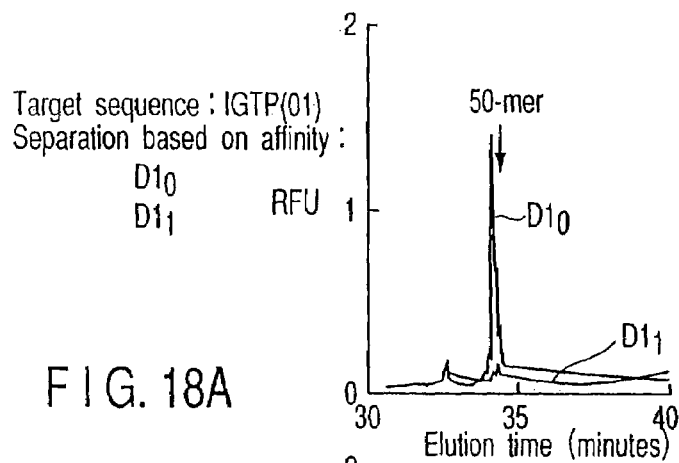
F I G. 18A
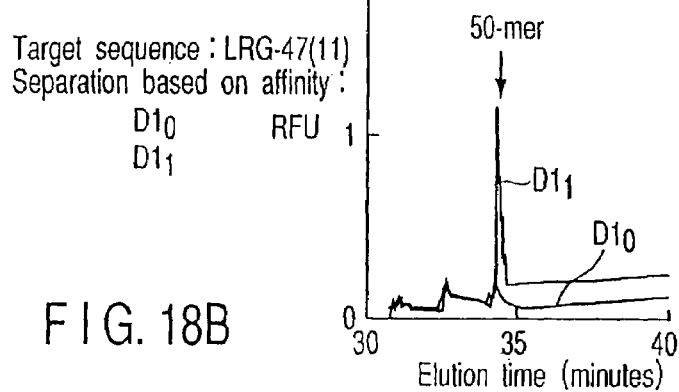
F I G. 18B
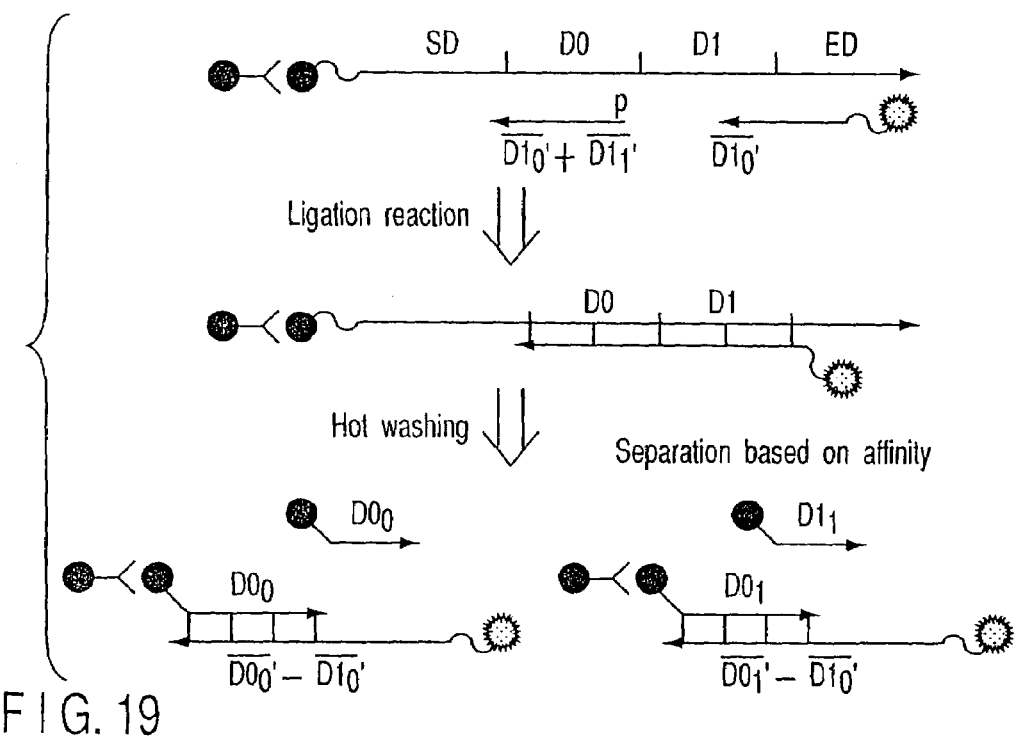
F I G. 19

SEQUENCE LISTING

<160> NUMBER OF SEQ ID NOS: 16

<210> SEQ ID NO 1
<211> LENGTH: 16
<212> TYPE: DNA
<213> ORGANISM: Artificial Sequence
<220> FEATURE:
<223> OTHER INFORMATION: Nucleic Acid Probe

<400> SEQUENCE: 1
ctagtagggt gaagtc                                                    16

```
<210> SEQ ID NO 2
<211> LENGTH: 64
<212> TYPE: DNA
<213> ORGANISM: Artificial Sequence
<220> FEATURE:
<223> OTHER INFORMATION: Nucleic Acid Probe

<400> SEQUENCE: 2
cataagagcc ctagagcatg ctggtcaagg ggcacgcggt tcatcaggag tcgaaggcag     60
gacg                                                                 64

<210> SEQ ID NO 3
<211> LENGTH: 32
<212> TYPE: DNA
<213> ORGANISM: Artificial Sequence
<220> FEATURE:
<223> OTHER INFORMATION: Nucleic Acid Probe

<400> SEQUENCE: 3
ctctagggct cttatggact tcaccctact ag                                  32

<210> SEQ ID NO 4
<211> LENGTH: 48
<212> TYPE: DNA
<213> ORGANISM: Artificial Sequence
<220> FEATURE:
<223> OTHER INFORMATION: Nucleic Acid Probe

<400> SEQUENCE: 4
cgtcctgcct tcgactcctg atgaaccgcg tgcccttga ccagcatg                  48

<210> SEQ ID NO 5
<211> LENGTH: 32
<212> TYPE: DNA
<213> ORGANISM: Artificial Sequence
<220> FEATURE:
<223> OTHER INFORMATION: Nucleic Acid Probe

<400> SEQUENCE: 5
ttctagagct cctatggact tcgccctact ag                                  32

<210> SEQ ID NO 6
<211> LENGTH: 30
<212> TYPE: DNA
<213> ORGANISM: Mouse

<400> SEQUENCE: 6
tcctatattc aactgtaata gcccgttcct                                     30

<210> SEQ ID NO 7
<211> LENGTH: 30
<212> TYPE: DNA
<213> ORGANISM: Mouse

<400> SEQUENCE: 7
attttcctct gaaacaataa agtcggttcc                                     30

<210> SEQ ID NO 8
<211> LENGTH: 15
<212> TYPE: DNA
<213> ORGANISM: Artificial Sequence
<220> FEATURE:
<223> OTHER INFORMATION: Nucleic Acid Probe
```

```
<400> SEQUENCE: 8
tcctatattc aactg                                                    15

<210> SEQ ID NO 9
<211> LENGTH: 15
<212> TYPE: DNA
<213> ORGANISM: Artificial Sequence
<220> FEATURE:
<223> OTHER INFORMATION: Nucleic Acid Probe

<400> SEQUENCE: 9
attttcctct gaaac                                                    15

<210> SEQ ID NO 10
<211> LENGTH: 15
<212> TYPE: DNA
<213> ORGANISM: Artificial Sequence
<220> FEATURE:
<223> OTHER INFORMATION: Nucleic Acid Probe

<400> SEQUENCE: 10
taatagcccg ttcct                                                    15

<210> SEQ ID NO 11
<211> LENGTH: 15
<212> TYPE: DNA
<213> ORGANISM: Artificial Sequence
<220> FEATURE:
<223> OTHER INFORMATION: Nucleic Acid Probe

<400> SEQUENCE: 11
aataaagtcg gttcc                                                    15

<210> SEQ ID NO 12
<211> LENGTH: 25
<212> TYPE: DNA
<213> ORGANISM: Artificial Sequence
<220> FEATURE:
<223> OTHER INFORMATION: Nucleic Acid Probe

<400> SEQUENCE: 12
tgaagtcacc acaacacaca gtaca                                         25

<210> SEQ ID NO 13
<211> LENGTH: 25
<212> TYPE: DNA
<213> ORGANISM: Artificial Sequence
<220> FEATURE:
<223> OTHER INFORMATION: Nucleic Acid Probe

<400> SEQUENCE: 13
tctcagtccc agtccatttc cttac                                         25

<210> SEQ ID NO 14
<211> LENGTH: 25
<212> TYPE: DNA
<213> ORGANISM: Artificial Sequence
<220> FEATURE:
<223> OTHER INFORMATION: Nucleic Acid Probe

<400> SEQUENCE: 14
acgacgatga aaaactacga gggac                                         25

<210> SEQ ID NO 15
<211> LENGTH: 25
```

-continued

```
<212> TYPE: DNA
<213> ORGANISM: Artificial Sequence
<220> FEATURE:
<223> OTHER INFORMATION: Nucleic Acid Probe

<400> SEQUENCE: 15
tgaaccccca agtttagatc tcagc                                            25

<210> SEQ ID NO 16
<211> LENGTH: 25
<212> TYPE: DNA
<213> ORGANISM: Artificial Sequence
<220> FEATURE:
<223> OTHER INFORMATION: Nucleic Acid Probe

<400> SEQUENCE: 16
gacaaacacc ccgaatacaa acagc                                            25
```

METHOD OF DETECTING NUCLEIC ACID

CROSS REFERENCE TO RELATED APPLICATIONS

This is a Continuation Application of U.S. patent application having Ser. No. 09/872,881 filed on Jun. 1, 2001, now abandoned, which is a continuation application of PCT Application No. PCT/JP00/06919, filed Oct. 4, 2000, which was not published under PCT Article 21(2) in English.

This application is based upon and claims the benefit of priority from the prior Japanese Patent Applications No. 11-283148, filed Oct. 4, 1999; and No. 11-283437, filed Oct. 4, 1999, the entire contents of both of which are incorporated herein by reference.

BACKGROUND OF THE INVENTION

The present invention relates to a method of detecting or quantifying a nucleic acid molecule present in a specimen.

Techniques for detecting a specific nucleic acid molecule present in a biological specimen are of importance in the fields of fundamental research and clinical study. The techniques are particularly important in analyzing proteins, which express and function at specific organs, at a nucleic-acid level. The techniques are also important in investigating expression of proteins and how to control the expression of proteins in the nervous system and the immune system associating signal transduction system. The techniques are extremely important in genetic diagnosis since mutant genes associated with genetic diseases, genes associated with cancer, and genes associated with viruses can be identified by these techniques.

A representative technique for detecting a nucleic acid molecule is a hybridization method. In this method, a target nucleic acid is hybridized with a nucleic acid probe having a complementary sequence of the target nucleic acid. Thereafter, the target nucleic acid can be identified using the probe. A drawback of this method resides in that it is difficult to detect a target nucleic acid if it is present in low numbers (e.g., about 1 to 1000 copies). Furthermore, the specificity is low. Therefore, it is difficult to recognize and detect analogous sequences distinguishably.

In a device called a DNA chip, various types of nucleic-acid probes are immobilized on a base. Detection using the detection method employing the DNA chip is much easier, compared to conventional hybridization methods. However, the probes immobilized on the base differ in optimal conditions, so that a false positive hybridization reaction may take place. This is a problem with this method. Furthermore, the design of the probe to be immobilized on the base must be changed in accordance with the nucleic acid to be detected. This means that an appropriate DNA chip must be prepared every time the nucleic acid to be detected is changed. Whereas, in clinical tests, various types of nucleic acids must be detected. Under these circumstances, conventionally a wide variety of DNA chips are required.

Conventional techniques, including the aforementioned methods, are complicated since an operation consists of many steps. In addition, a long detection time and a well-trained operator are required.

Gene diagnosis is usually used as a definite diagnosis. Therefore, a quick diagnosis is required without the possibility of miss-diagnosis. However, conventional methods do not fully satisfy these requirements.

BRIEF SUMMARY OF THE INVENTION

An object of the present invention is to provide a method of detecting a target nucleic acid molecule from a specimen, with a high specificity. According to the present invention, it is possible to detect and quantify only a specific nucleic acid accurately and quickly from a specimen containing a plurality of types of nucleic acid molecules.

Another object of the present invention is to provide a method of detecting a target sequence which is present few in number, thereby saving the number of DNA chips required. A further object of the present invention is to provide a method which can be easily carried out in a few steps.

The aforementioned objects can be attained by the present invention shown below.

There is provided a method of detecting or quantifying a target nucleic acid having a predetermined sequence in a specimen, comprising:

(a) preparing a probe A and a probe B:

the probe A is a first probe including a complementary sequence F' to a first partial sequence F of the target nucleic acid and a binding molecule connected to the sequence F'; and the probe B is a second probe including a complementary sequence S' to a second partial sequence S of the target nucleic acid and a flag linked to the sequence S', in which the flag is a double-stranded sequence one of which includes a marker substance;

(b) hybridizing the first partial sequence F of the target nucleic acid with the first probe A and hybridizing the second partial sequence S with a second probe B;.

(c) linking the first probe A and the second probe B, both being hybridized with the target nucleic acid molecule, thereby producing a probe (A+B);

(d) linking a substrate capable of being paired up with the binding molecule and having a high affinity with the binding molecule, to the binding molecule, thereby recovering the probe (A+B); and (e) recovering a single-stranded nucleic acid containing the marker substance from the nucleic acids constituting the flag, and detecting or quantifying the marker substance, thereby detecting or quantifying the target nucleic acid from the specimen.

Two probes are employed to detect the target nucleic acid in the method of the present invention. Therefore, in this method, a stable hybridization can be performed while preventing a non-specific binding. Furthermore, the target nucleic acid can be identified by detecting the probe (A+B). Therefore, the detection can be made with a high sequence-specificity and a high detection accuracy.

Furthermore, in the present invention, a target nucleic acid is detected by detecting the flag. The advantage of the present invention basically resides in obtaining information regarding a target nucleic acid by substituting the information with the flag, and then detecting or analyzing the flag, as is explained later. An operator can design the flag appropriately. Hence, no matter what type of nucleic acid is used as a detection target, a common DNA chip is indiscriminately used for detection without preparing DNA chips varied depending upon detection targets. It is therefore possible to save the number of DNA chips required. Furthermore, the number of probe types to be immobilized on the DNA chip can be reduced. If the design of the flag is modified, the detection efficiency of a target nucleic acid can be tremendously improved. Simultaneously, the detection step can be simplified.

For example, if the flag is designed so as to have a stable nucleic acid sequence, stable detection results can be obtained. The flag may be constituted of a plurality of units. In the case where a plurality of units are used, it is possible to encode the information of the target nucleic acid. A wide variety of information items of a target nucleic acid can be converted into codes which vary depending upon the combination of the plural units contained in the flag sequence. Furthermore, if the code is constructed with DNA sequence, the DNA code itself can be amplified (nucleotide sequence). If the DNA code uniform in length and stability is amplified by using the same primer pair, the quantification of DNA can be excellently made compared to the conventional method of amplifying a target nucleic acid itself. Therefore, a target sequence can be accurately detected and quantified, even if it is present in low numbers of copies. If it is devised that the DNA code is converted to a numerical value by using a specific algorithm, a calculation based on a DNA molecular reaction can be attained. By such a conversion, the analysis of personal genetic information such as blood types and SNPS can be simplified. In the present invention, it is possible to read out the information of a target nucleic acid from codes of the aforementioned units.

Furthermore, a further object of the present invention is to provide a method of simultaneously detecting a plurality of types of target nucleic acids from a specimen in a simple operation.

To attain the object, probes A1 to An (n is an integer of 2 or more) as well as probes B1 to Bn (n is an integer of 2 or more) are prepared with respect to the corresponding target nucleic acids N1 to Nn (n is an integer of 2 or more) and the aforementioned steps are repeated in the same manner as above. According to the present invention, individual target nucleic acids can be simply and easily detected with a high specificity. When a plurality of types of target nucleic acids are detected, the use of a flag is particularly useful.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a flow chart showing Example 2 of the present invention;

FIG. 7A is a table showing examples of flag design used in the present invention and FIG. 7B shows a diagram showing the detection device corresponding to the design of FIG. 7A;

FIG. 8 is a schematic diagram showing a binding state of a target nucleic acid and a probe in the evaluation test of Example 1 of the present invention;

FIG. 9 shows probes A and B, target sequence, detection sequence and a modified sequence (SEQ ID NOs: 1-5 respectively);

FIG. 13A shows two probes A and B, and a target sequence used in the evaluation test of Example 5 of the present invention (SEQ ID NOs: 6-16 respectively);

FIG. 13B is a view showing individual probes and elements constituting the probes;

FIGS. 14A and 14B are graphs showing a specificity of an encode reaction of the present invention;

FIG. 15 is a scheme of an experiment for evaluating characteristics of the encode reaction of the present invention;

FIGS. 18A and 18B are graphs showing the specificity and quantitative properties of a decode reaction of the present invention; and FIG. 19 is a scheme for conforming that decode reaction is performed specifically and quantitatively showing specificity and quantitative characteristics of a decode reaction of the present invention.

DETAILED DESCRIPTION OF THE INVENTION

The term "nucleic acid" used herein refers to all DNAs including cDNA, genomic DNA, and synthetic DNA; and all RNAs including mRNA, total RNA, hnRNA and synthetic RNA.

The term "target nucleic acid" refers to, but not limited to a nucleic acid having an arbitrary sequence. Examples of preferable "target nucleic acid" are nucleic acids of causal genes for genetic diseases, oncogenes, and virus-derived nucleic acids, which may act as a marker for disorders.

The term "binding pair" is a pair of substances capable of specifically binding to each other. For example, avidin and biotin; streptoavidin and biotin; and digoxigenin and a digoxigenin antibody. However, the binding pair is not limited to these. Any pair of substances may be used as long as they mutually bind to each other. In the case of avidin and biotin, the phrase "one of the binding pair" means either avidin or biotin. The term "the other one of the binding pair" means the remaining one. The term "binding molecule" used herein can be interchangeably used with the term "one of the binding pair" or "the other one of the binding pair". Similarly, the term "a molecule having a high affinity with the binding molecule" or the term "a molecule specifically binding to the binding molecule" may be interchangeably used with the term "one of the binding pair" or "the other one of the binding pair".

The term "specimen" used herein refers to, but not limited to a body fluid including blood, urine, saliva, and the like. Any specimen other than the body fluid may be included. For example, when the specimen is a solid matter, it may be converted into a liquid by an appropriate method including the addition of an enzyme, surfactant or an organic solvent.

The term "complementary sequence" used herein refers to a sequence capable of hybridizing specifically with a predetermined target nucleic acid alone under appropriate conditions.

EXAMPLE 1

Detection Method

Figure 1:
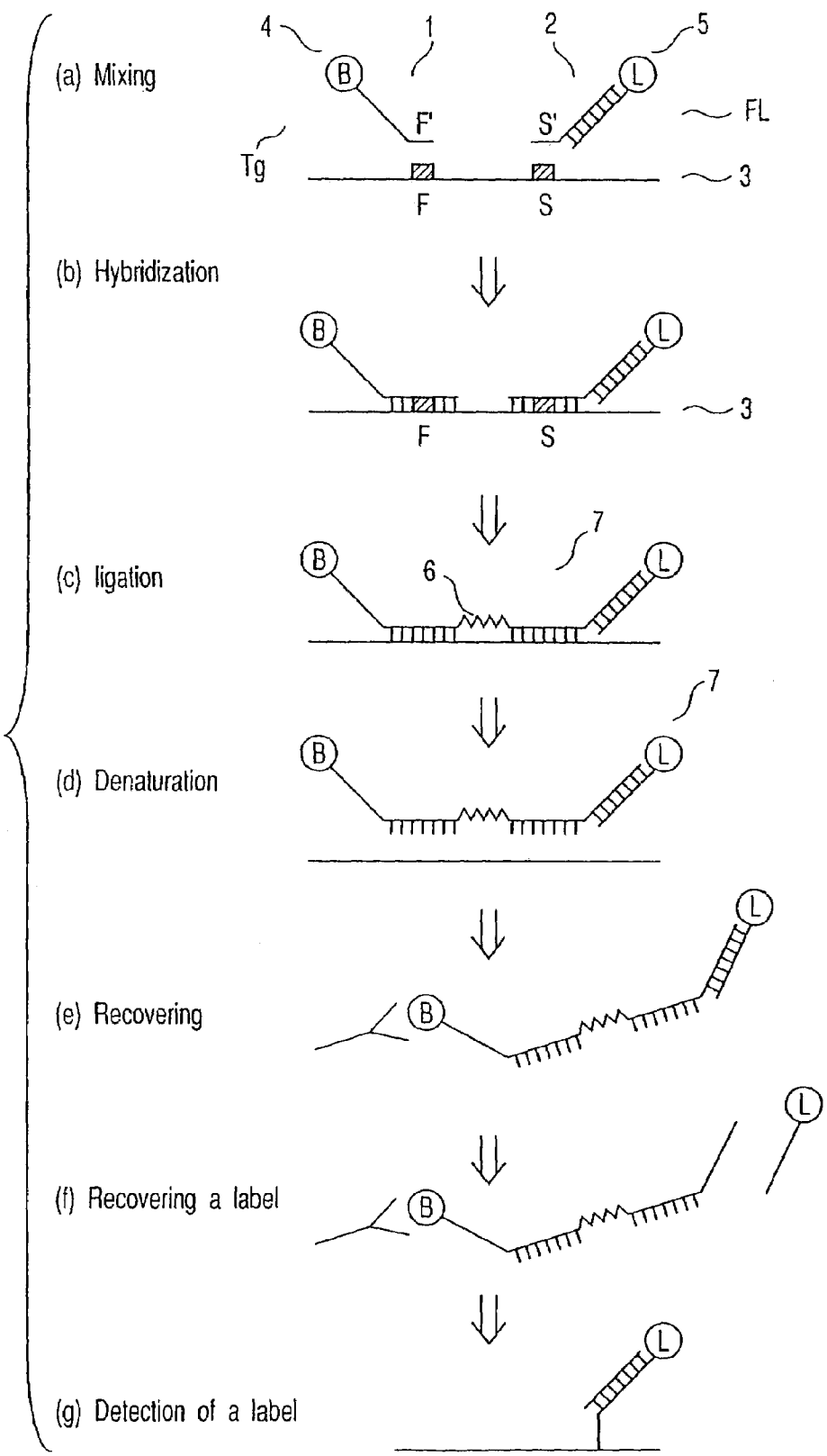
FIG. 1 is a flow chart showing Example 1 of the present invention.

A detection method of the present invention will be explained with reference to FIG. 1 (FIG. 1).

In the method of this example, two types of nucleic acid probes. (hereinafter, sometimes simply referred to as "probe") shown below, a probe A1 and a probe B2, are used (FIG. 1a).

The probe A1 is constituted of a sequence F' and a binding molecule 4 bound to the sequence F'. The sequence F' is complementary to a nucleotide sequence F of a partial region of the target nucleic acid 3. The binding molecule 4 used herein may directly bind to the sequence F' or indirectly bind to the sequence F' via some portion such as an arbitrary nucleotide sequence. The portion except the nucleotide sequence F of the probe A1 may be referred to as a "tag", "tag sequence Tg" or "Tg". The arbitrary sequence, which is responsible for the indirect binding, may be a nucleotide sequence having any number of nucleotides. More preferably, the sequence may be a non-complementary sequence to the nucleotide sequence of the target nucleic acid. Alternatively, the indirect binding may be mediated by other means such as chemical or physical means. The tag Tg is required to neither bind to nor interact with any portion of the target nucleic acid. The term "non-complementary" used herein refers to a nucleotide sequence which does not hybridize with a sequence of the target nucleic acid, in particular, a sequence within an arbitral range for use in detection.

The sequence F' used herein has a nucleotide of 1 or more. The sequence F' preferably has 15 or more of nucleotides to attain stable hybridization.

The binding molecule 4 used herein may be either one of the pair molecules specifically binding to each other, as previously described.

The probe B2 consists of a sequence S' and a flag (hereinafter, sometimes represented by "FL") bound to the sequence S'. The sequence S' is complementary to a nucleotide sequence S, which is a part of the target nucleic acid 3. In this example, the flag consists of a double-stranded sequence linking to the sequence S' and the marker substance 5 bound to the double stranded sequence. Generally, it is necessary that the flag itself neither binds to nor interacts with the target nucleic acid 3. Therefore, when the flag is a nucleotide sequence, the entire length is not necessarily formed of a double-strand nucleic acid. The flag may be formed of a single-stranded sequence in part or in its entirety as long as it neither binds to nor interacts with the target nucleic acid. Furthermore, the flag has any number of nucleotides. Alternatively, the marker substance 5 may be bound to the sequence S' by any means, as detailed in Example 3 set forth later.

When the flag is a double-stranded sequence, the sequence may be formed of any types of nucleotides and may have any number of nucleotides. However, the Tm of the sequence must be sufficiently higher than those of the sequence F and the sequence S. Particularly in the case where the flag has a double-stranded sequence, the flag sequence is not directly bound to the sequence S'. More specifically, the flag sequence hybridizes with the sequence which directly bounds to the sequence S'.

As the marker substance 5 used herein, any substance is used as long as it is generally used as a marker substance. Preferable examples of the marker substance include fluorescent substances, luminescent substances, radioisotope substances such as $^{32}P$, high absorbency substances, high reflection substances, high potential substances, magnetic substances, and pigments. Particularly, fluorescent substances such as FITC are preferable.

The sequence S' used herein has nucleotide(s) of 1 or more, preferably 15 or more.

Tg attached to the probe A1 and FL attached to the probe B2 are preferably designed so as to be positioned at ends at the farthest distance from each other when both probes are bound to the desired regions of the target nucleic acid 3, as shown in FIG. 1b.

The probe A1 and probe B2, when they bind to the desired regions of the target nucleic acid 3, preferably have the nucleotides complementary to adjacent nucleotides on the target nucleic acid 3, at the close ends. This is advantageous in a ligation step performed thereafter. However, this is not limited thereto.

The sequences F and S of the probes A1 and B2 may be appropriately selected so as to have the same Tm by controlling the conditions including the GC content and the combination of nucleotide bases.

The example is carried out as described below. First, the probe A1 and probe B2 are prepared in accordance with the target nucleic acid 3. They are mixed, at an appropriate ratio, with the target nucleic acid 3 (FIG. 1a).

Subsequently, the mixture is incubated under arbitrary conditions suitable for hybridization for a predetermined time period to perform hybridization (FIG. 1b).

The hybridization is performed by any general method. The preferable hybridization is performed by allowing the mixture stand still at an appropriate high temperature, for example, 95° C., effective in denaturing a nucleic acid, for 5 minutes, whereby the complimentary binding of the target nucleic acid is dissociated to convert a double strand to a single strand. In the case of the single-stranded target nucleic acid, the single-strand target nucleic acid is allowed to stand still at 70° C. for 5 minutes, whereby it can be converted into a secondary structure. Subsequently, the single-strand is allowed to stand still at an appropriate temperature effective in rebinding of a complementary nucleotide sequence, for example, 55° C. for 15 minutes, the single-stranded target nucleic acid is rebound to the complementary nucleotide sequence. By the hybridization process mentioned above, both the probes A1 and B2 bind to the same target nucleic acid 3 to make a hybrid. Therefore, it is not necessary that conditions including the type of buffer and temperature are limited to those mentioned above. Any conditions may be employed as long as the probes A1 and B2 are hybridized with the target nucleic acid 3 under the conditions.

Thereafter, the probe A1 is linked with the probe B2 (FIG. 1c). In the present invention, the probe A1 and the probe B2 both being hybridized on the target nucleic acid 3 are linked to each other, to form a probe (A+B) 7. This linkage is attained by formation of the linkage portion 6.

This linkage is made by use of Taq DNA ligase such as Thermus aquatius (Taq) DNA ligase manufactured by New England Biolab. However, the agent used in this linkage is not limited to this. Any agent may be used as long as it is generally used in the linkage. Furthermore, both probes may be linked with any chemical means in place of the enzymatic means.

When the sequences F and S are not present on the target nucleic acid 3 next to each other, a gap-filling reaction may be performed by using DNA polymerase I and a ligase. By this reaction, nucleotides may be introduced in the gap between both proves. Any DNA polymerase and ligase may be used as long as they are generally used. Preferably, heat-resistance DNA polymerase and ligase are preferable.

Subsequently, a probe (A+B) 7 obtained in the above is dissociated from a target nucleic acid 3 (FIG. 1d). The dissociation may be performed by denaturation treatment such as thermal denaturation. More specifically, when the dissociation is performed by thermal denaturation, the reaction may be made, but not limited to, under physiological conditions at 85° C. or more, preferably 90° C. or more. However, when the flag sequence is a double strand, the dissociation may be made of a temperature lower than the melting temperature, Tm, of double strand.

Subsequently, a binding molecule 4, that is, one of the binding pair, is allowed to bind to a molecule having a high affinity with the binding molecule. In this manner, a prove (A+B) 7 is recovered (FIG. 1e). Subsequently, the flag is denatured and converted into a single chain. The single strand tagged with the marker substance 5 is allowed to hybridize with a sequence complementary to the single strand (FIG. 1g). In this way, the single strand is recovered. Thereafter, the marker substance 2 is detected or quantified, whereby detection or quantification of the target nucleic acid (FIG. 1g) is completed. The detection may be performed by any general method suitable for the marker substance used herein.

A single strand having the probe (A+B) 7 and the marker substance 5 bound thereto is separated by Bound/Free separation (hereinafter, referred to as "B/F separation"). Therefore, the accuracy in detection is improved. The B/F separation is performed in accordance with the B/F separation method generally employed.

In this method, the B/F separation for the single strand tagged with the marker substance 5 may be. preferably performed using a solid-phase carrier having a nucleotide sequence complementary to the single strand fixed on an appropriate support (FIG. 1g). The B/F separation for the probe (A+B) 7 can be preferably performed by a solid-phase carrier having a molecule capable of specifically binding to the binding molecule 4 immobilized on an appropriate support (FIG. 1e).

Examples of the support to be used include, but not limited to, a substrate such as a silicon plate or a glass plate, particles such as beads, a container such as a test tube or a vial, a fiber, a tube including a capillary, a filter, an affinity column, an electrode and the like. It is preferable that the material of the support and surface treatment be appropriately selected depending upon how efficiently the probe is fixed.

Since the flag has an artificially synthesized sequence, the sequence may be designed such that it has properties for improving the specificity of the hybridization of the probe (A+B).

EXAMPLE 2

Example of Detection Method

This method is also effective when a plurality of target nucleic acids are simultaneously detected. FIG. 2 shows the case where a plurality of target nucleic acids N1, N2, N3 ... Nn (hereinafter referred to as "N1-Nn") where n is an integer of 2 or more) are simultaneously detected.

Individual steps and the constitutions of individual probes are the same as in Example 1 except that a plurality of detection targets are used (FIG. 2, a to e).

To-explain more specifically, target nucleic acids N1-Nn, probes A1-An, and probes B1-Bn are mixed (FIG. 2a). They are allowed to hybridize with the target nucleic acids, respectively, and then the probes A1-An are linked to the probes B1-Bn, respectively (FIG. 2b). The resultant probes (A1+B1)-(An+Bn) are dissociated from the target nucleic acids (not shown). Then, the probes (A1+B1)-(An+Bn) dissociated are recovered (FIG. 2c). Each of the flags is denatured to obtain a single strand (FIG. 2d). The single strand having a marker substance attached thereto is recovered and the marker substance is detected or quantified (FIG. 2e). The plurality types of target nucleic acids can be simultaneously detected or quantified by using the same marker substance. Therefore, this method made it easier to detect a plurality of target nucleic acids in fewer steps than those of conventional methods.

To distinguish a plurality of target nucleic acids by using the same marker substance, the flags having different sequences modified depending upon the target nucleic acids may be used. Furthermore, as shown in FIG. 2(e), when complementary sequences, which are used for recovering target single strands, are immobilized to the substrate, they may be placed in different regions depending upon the sequences. It may be possible to modify the sequences of the flags simultaneously with the immobilization of the complementary sequences in different regions.

Alternatively, it is possible to use different marker substances depending upon the target nucleic acids. In this case, the modification of the flag and the immobilization of the complementary sequences in different regions are not necessarily performed.

If the GC contents of Fn' and Sn' sequences of a probe (A1+B1), (A2+B2) ... (An+Bn) [hereinafter, referred to as "(A1+B1)-(An+Bn)"] and the types of nucleotides are appropriately selected, optimal hybridization conditions (e.g., temperature and salt concentration) which differ between individual probes can be overcome. When a plurality of types of flags different in sequence are used, it is preferable to use the same (common) hybridization conditions even if the types of flags differ. In this manner, detection accuracy is improved. The detection accuracy is further improved by increasing the common Tm value of the flag sequences sufficiently higher than those of the sequences Fn' and Sn'.

In contrast, in the conventional nucleic acid detection method, in which a complementary sequence of the target nucleic acid is immobilized, optimal hybridization conditions for individual probes immobilized differ in general. However, it is impossible to set the conditions suitable for all probes.

EXAMPLE 3

Example of Detection Method

Figure 3:
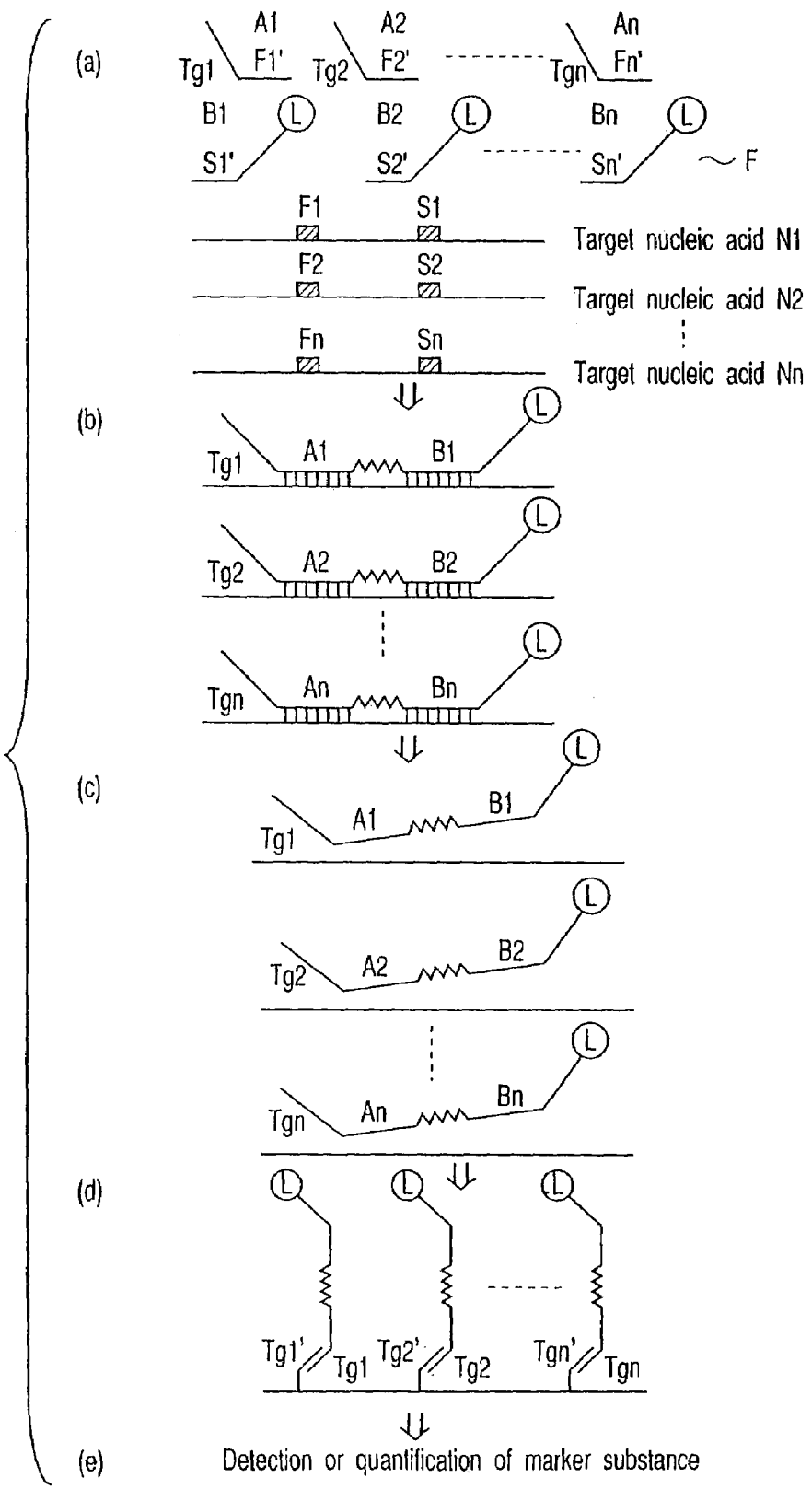
FIG. 3 is a flow chart showing Example 3 of the present invention.

Referring to FIG. 3, another example of the present invention will be explained. In the method of this example, a plurality of target nucleic acids N1, N2, N3 ... Nn (Hereinafter, referred to as N1-Nn where n is an integer of 2 or more) can be simultaneously detected. Probes A1, A2, A3 ... An (hereinafter referred to as "A1-An" where n is an integer of 2 or more) and probes B1, B2, B3 ... Bn (hereinafter referred to as "B1-Bn" where n is an integer of 2 or more) are prepared corresponding to the target nucleic acids N1-Nn. These nucleic acid probes have the characteristics shown below (FIG. 3a).

The probes A1-An are formed of sequences F1' to Fn', and tag Tg1 to Tgn (hereinafter referred to as "Tg1-Tgn") bound to the sequences F1' to Fn', respectively. The sequences F1' to Fn' are complementary to nucleotide sequences F1 to Fn, which are parts of the target nucleic acids N1-Nn, respectively. The tag Tg1 to Tgn (hereinafter referred to as "Tg1'-Tgn') of this example are nucleotide sequences. Each of the sequences of the tags Tg1-Tgn is required not to bind to and thus not to interact with any portion of its target nucleic acid. The tags Tg1 to Tgn used herein may be directly bound to respective sequences F1' to Fn' or indirectly bound to them via any intermediate portion, for example, a nucleotide sequence. When the tags are indirectly bound via an nucleotide sequence arbitrarily chosen, the arbitrary sequence may be any nucleotide sequence having any number of nucleotides. The nucleotide sequence is preferably non-complementary to the nucleotide sequence of a target nucleic acid. They may be bound by a chemical or physical means.

The sequences F1' to Fn' used herein have nucleotides different from each other. They may be nucleotides of one or more. To attain stable hybridization, the sequences preferably have nucleotide of 15 or more.

As shown in FIG. 3a, the probes B1-Bn are formed of sequences S1' to Sn' and arbitrary flags (hereinafter referred to as "FL") bound to the sequences S1' to Sn'. The sequences S1' to Sn' are complementary to respective nucleotide sequences Si to Sn, which are parts of respective target nucleic acids. In this example, the flags contain a marker substance. The flags themselves do not bind to, and thus interact with the target nucleic acids, in the same as in the previous examples. The probes B1-Bn of this example are constructed by binding the marker substance to the sequences S1' to Sn' by an arbitrary means.

As the marker substance used herein, any substance may be used as long as it is a marker substance generally used, as set forth in Example 1. More preferably, each of the sequences S1' to Sn' has nucleotides of 15 or more.

When probe A1(An) and probe B1(Bn) are bound to respective desired regions of the target nucleic acid, as shown in FIG. 3b, the end of the probe A1(An) having the tag attached thereto and the end of the probe B1(Bn) having the flag attached thereto, are preferably positioned at the farthest distance from each other (FIG. 3b). Furthermore, when the probe A1(An) and probe B1(Bn) are bonded to respective desired regions of the target nucleic acid, the nucleotides positioned at proximal ends of both probes are preferably complementary to the nucleotides positioned next to each other on the target molecule. This positioning is advantageous in a ligation step performed later. However, the positioning of the complementary nucleotides is not limited thereto.

If the GC content and the nucleotide types of sequences F1'-Fn' and S1'-Sn' contained in these probes are appropriately selected, it is possible to overcome the differences in optimal hybridization conditions of individual probes. When a plurality of types of tag sequences are used, it is preferable that they can be hybridized well under the same (common) hybridization conditions. Furthermore, if the common Tm value of the tag sequences is set sufficiently higher than those of the Fn' and Sn' sequences, the detection accuracy is improved.

This example is carried out in the following manner. First, probes A1-An and probes B1-Bn are prepared in accordance with the target nucleic acids N1-Nn, as mentioned above. Then, they are mixed with the target nucleic acids N1-Nn, in an appropriate ratio (FIG. 3a).

Then, the mixture is incubated for a predetermined time under arbitrary conditions suitable for hybridization. In this manner, hybridization is performed (not shown).

The hybridization may be performed by any general method. Preferable hybridization is performed as follows. First, a target nucleic acid is allowed to stand still at a high temperature, for example, 95° C., which is effective in denaturing the target nucleic acid. In the step, the complementary binding of the target nucleic acid is denatured, with the result that a double strand is dissociated into a single strand. In the case where the target nucleic acid is a single strand, the nucleic acid is allowed to stand still at 70° C. for 5 minutes to denature its secondary structure. Subsequently, the resultant reaction mixture is allowed to stand still for 15 minutes at an appropriate temperature, e.g., 55° C. which is effective in rebinding a complementary nucleotide sequence. As a result, the single-stranded nucleic acid is rebound to the complementary nucleotide sequence.

By the hybridization step, each set of probes A1-An and probes B1-B2 bind to the same and corresponding target nucleic acid to produce hybrids. Accordingly, type of a buffer solution to be employed and temperature condition are not limited to those mentioned above. Any conditions may be employed as long as the probes A1-An and probes B1-Bn can hybridize with respective target nucleic acids.

Subsequently, the probes A1-An are bound the corresponding probes B1-Bn (FIG. 3b). More specifically, in the present invention, the probes A1-An and probes B1-Bn both being hybridized on the respective target nucleic acids N1-Nn are respectively ligated, producing probes (A1+B1) to (An+Bn), respectively. The ligation is attained by forming a ligation portion. The ligation may be performed in the same manner as Example 1.

Furthermore, in the case where the sequence F and the sequence S are not placed next to each other on the target nucleic acid, the gap between them may be filled by use of DNA polymerase I and a ligase. In this way, nucleic acid bases are introduced into the gap between both probes. Any DNA polymerase I and ligase may be used as long as they are generally used. Heat resistant DNA polymerase and ligase are preferably used.

Subsequently, the probes (A1+B1) to (An+Bn) obtained above are dissociated from the target nucleic acids (FIG. 3c). The dissociation is performed by denaturation treatment such as thermal denaturation. For example, when the dissociation is performed by the thermal denaturation, the reaction is performed under physiological conditions at 85° C. or more, preferably, 90° C. or more. However, the conditions are not limited thereto.

The probes (A1+B1) to (An+Bn) are recovered by using the sequences Tg1' to Tgn' which hybridize with complementary sequences Tg1 to Tgn (FIG. 3d). Thereafter, the marker substance is detected or quantified. In this manner, the target nucleic acids can be detected or quantified (FIG. 3d). A detection method varies depending upon the marker substance and any detection method may be used as long as it is generally used.

The complementary sequences Tg1' to Tgn' are preferably fixed on a support. Examples of the support to be used include, but not limited to, a substrate such as a silicon plate or a glass plate, particles such as beads, a container such as a test tube or a vial, a fiber, a tube including a capillary, a filter, an affinity column, an electrode and the like. It is preferable that the material of the support and surface treatment be appropriately selected depending upon how efficiently the probe is fixed.

In Example 3, a plurality of target nucleic acids are used. However, the method used herein is applicable to a single target nucleic acid. If the number of types of the marker substances are increased, a larger number of target nucleic acids can be identified.

EXAMPLE 4

Figure 4:
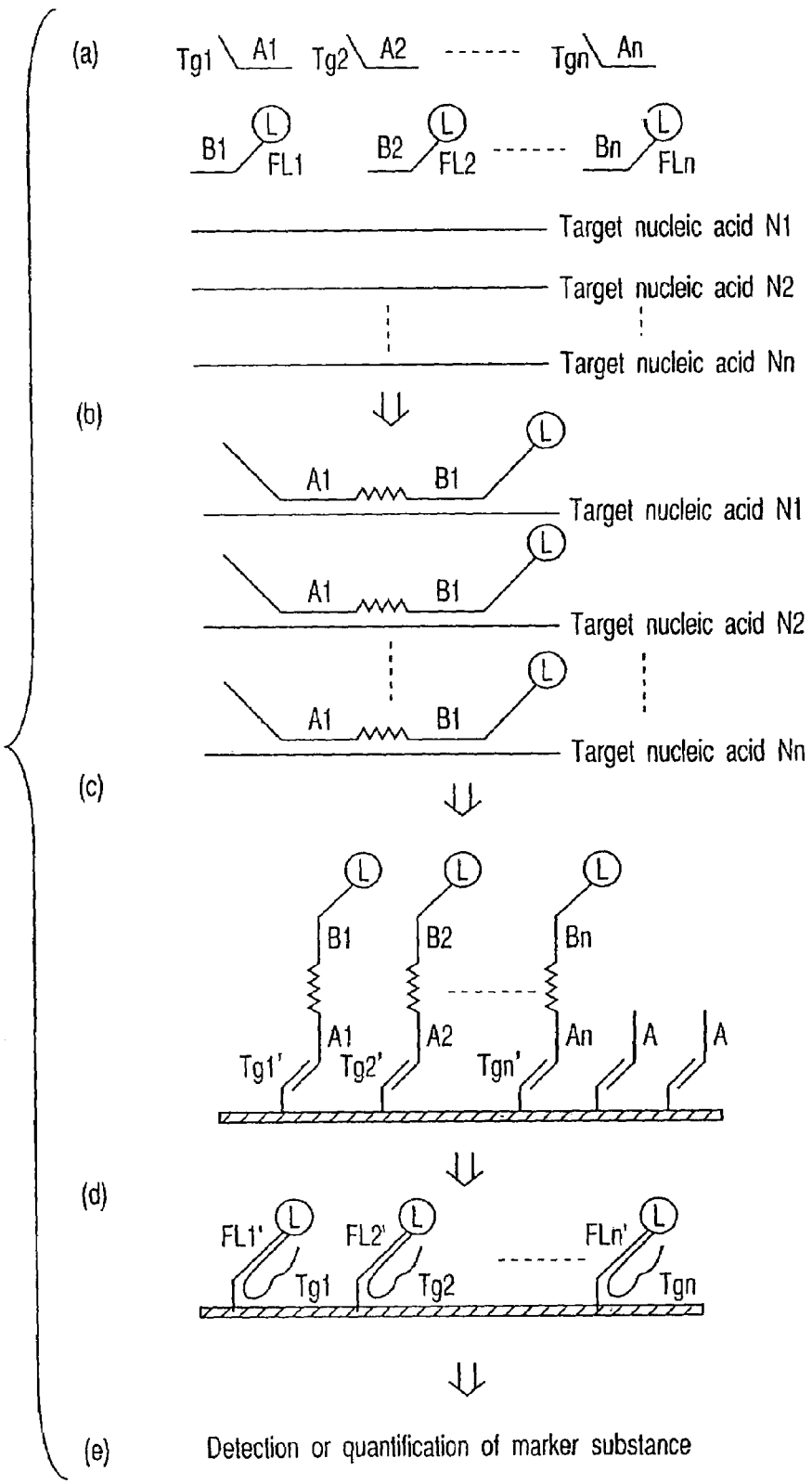
FIG. 4 is a flow chart showing Example 4 of the present invention.

Referring now to FIG. 4, another example of the present invention will be explained. In the method of this example, a plurality of target nucleic acids N1, N2 N3 . . . Nn (hereinafter, referred to as "N1-Nn" where n is an integer of n or more) are simultaneously detected. Probes A1, A2 A3 . . . An (hereinafter, referred to as "A1-An" where n is an integer of 2 or more) and probes B1, B2, B3 . . . Bn (hereinafter, referred to as "B1-Bn" where n is an integer of 2 or more) are prepared corresponding to the target nucleic acids N1-Nn. These probes have the following characteristics (FIG. 4a).

The probes A1-An is formed of sequences F1' to Fn' and tags Tg1 to Tgn bound to the sequences F1' to Fn', respectively. The sequences F1' to Fn' are complementary to nucleotide sequences F1 to Fn, which are part of the target nucleic acids N1-Nn, respectively. Tags Tg1 to Tgn of this example are nucleotide sequences which do not bind to any portion of the corresponding target nucleic acids and do not exhibit any interactions with the target nucleic acids. Tags Tg1 to Tgn may directly bind to the respective sequences F1' to Fn' and indirectly bind to them via an intermediate portion such as a nucleotide sequence. In the case of the indirect binding via an sequence arbitrarily chosen, the sequence may consist of any types of nucleotides and any number of nucleotides. Preferably, the sequence is non-complementary to the nucleotide sequence of the target nucleic acid. Alternatively, they may bind to each other by a chemical or physical means.

The sequences F1' to Fn' used herein are different each other. They may be nucleotides of one or more. To attain a stable hybridization, the sequences F1' to Fn' preferably have nucleotides of 15 or more.

As shown in FIG. 4a, the probes B1-Bn have sequences S1' to Sn' and flags bound to the sequences S1 ' to Sn', respectively. The sequences S1' to Sn' are complementary to nucleotide sequences S1 to Sn of parts of the target nucleic acids, respectively. The flags have nucleotide sequences FL to FLn and a marker substance, respectively. As is the same as in Examples mentioned above, the flags themselves do, not bind to the target nucleic acids and do not exhibit any interactions with the target nucleic acids. The probes B1-Bn are constructed by binding the marker substance to the sequences S1' to Sn' by an arbitrary means.

As the marker substance used herein, any substance may be used as long as it is generally used as a marker substance, as described in Example 1.

The sequence S' used herein has nucleotides of 1 or more, preferably 15 or more.

When probe A1(An) and probe B1(Bn) are bound to respective desired regions of the target nucleic acid, as shown in FIG. 4b, the end of the probe A1(An) having the tag attached thereto and the end of the probe B1(Bn) having the flag attached thereto, are preferably positioned at the farthest distance from each other (FIG. 4b). Furthermore, when the probe A1(An) and probe B1(Bn) are bonded to respective desired regions of the target nucleic acid, the nucleotides positioned at proximal ends of both probes are preferably complementary to the nucleotides positioned next to each other on the target molecule. This positioning is advantageous in a ligation step performed later. However, the positioning of the complementary nucleotides is not limited thereto.

If the sequences F1'-Fn' and S1'-Sn' included in the probes are constructed by appropriately setting the GC content and the combination of nucleic acid bases, hybridization of the probes can be appropriately performed by overcoming different-optimal hybridization conditions of individual probes. When a plurality of types of tag sequences and flag sequences are used, it is preferable that they can be hybridized under the same (common) hybridization conditions. Furthermore, if the common Tm values of the tag sequences and flag sequences is set sufficiently higher than those of the sequences Fn' and Sn', the detection accuracy is improved. Furthermore, if a plurality of flag sequences are used with respect to a single tag sequence, the number of the target nucleic acids distinguishable from each other can be tremendously improved.

This example can be carried out in the following manner. First, the probes A1-An and probes B1-Bn are prepared in accordance with the target nucleic acids N1-Nn, as mentioned above. Then, the probes are mixed with the target nucleic acids N1-Nn in an appropriate ratio (FIG. 4a).

Subsequently, the mixture is incubated for a predetermined time under arbitrary conditions suitable for hybridization. In this manner, hybridization is performed (not shown).

The hybridization may be performed in any general method. Preferable hybridization is performed as follows. First, a target nucleic acid is allowed-to stand still at a high temperature, for example, 95° C., which is effective in denaturing the target nucleic acid. In the step, the complementary binding of the target nucleic acid is denatured, with the result that a double strand is dissociated into a single strand. Subsequently, the single-stranded nucleic acid is allowed to stand still for 15 minutes at an appropriate temperature, e.g., 55° C. which is effective in rebinding a complementary nucleotide sequence,. As a result, the single-stranded nucleic acid is rebound to the complementary nucleotide sequence.

By the hybridization step, each set of probes A1-An and probes B1-Bn bind to the same and corresponding target nucleic acid to produce hybrids. Accordingly, the type of a buffer solution to be employed and temperature conditions are not limited to those mentioned above. Any conditions may be employed as long as the probes A1-An and probes B1-Bn can hybridize with respective target nucleic acids.

Subsequently, the probes A1-An are bound the corresponding probes B1-Bn (FIG. 4b). More specifically, in the present invention, the probes A1-An and probes B1-Bn, both being hybridized on the respective target nucleic acids N1-Nn, are respectively ligated, producing probes (A1+B1) to (An+Bn), respectively. The ligation is attained by forming a ligation portion. The ligation may be performed in the same manner as Example 1.

Furthermore, in the case where the sequence F and the sequence S are not placed next to each other on the target nucleic acid, the gap between them may be filled by use of DNA polymerase I and a ligase. In this way, nucleic acid bases are introduced into the gap between both probes. Any DNA polymerase I and ligase may be used as long as they are generally used. Preferably, heat resistant DNA polymerase and ligase are used.

Subsequently, the probes (A1+B1) to (An+Bn) obtained above are dissociated from the target nucleic acids (not shown). The dissociation is performed by denaturation treatment such as thermal denaturation. For example, when the dissociation is performed by the thermal denaturation, the reaction is performed under physiological conditions at 85°

C. or more, preferably, 90° C. or more. However, the temperature conditions are not limited thereto.

The probes (A1+B1) to (An+Bn) are recovered by using the sequences Tg1' to Tgn' which hybridize with complementary sequences Tg1 to Tgn (FIG. 4c). Subsequently, the probes are dissociated by denaturation. The dissociated probes are recovered by hybridizing them respectively with the sequences FL' to FLn' complementary to the sequences FL1 to FLn (FIG. 4d).

Subsequently, respective marker substances are detected or quantified to detect and quantify the target nucleic acid (FIG. 4e). The detection method varies depending upon the marker substance and any detection method may be used as long as it is generally used.

The complementary sequences Tg1' to Tgn' and FL' to FLn' used herein are preferably fixed on a support. Examples of the support to be used include, but not limited to, a plate such as a silicon plate or a glass plate, particles such as beads, a container such as a test tube or a vial, a fiber, a tube including a capillary, filter, an affinity column, an electrode and the like. It is preferable that the material of the support and surface treatment may be appropriately selected depending upon how efficiently the probe is fixed.

EXAMPLE 5

Example of Detection Method

Now, a further preferable example of the present invention will be explained. If an appropriately designed flag is employed in the following method, a plurality of target nucleic acids can be efficiently detected with a high accuracy.

The following two types of nucleic acid probes, a probe A and a probe B, can be used in this method (FIG. 5a).

The probe A is formed of a nucleotide sequence F' and a binding molecule bound to the sequence F'. The sequence F' is complementary to a nucleotide sequence F which is a partial region of the target nucleic acid.

The binding molecule used herein is either one of two substances having specifically a high affinity with each other. For example, biotin, avidin, or streptoavidin. Furthermore, the binding molecule may bind directly to the sequence F' or may be indirectly bind to the sequence F' via an arbitrary sequence. The arbitrary sequence, which is responsible for the indirect binding, may be any nucleotide sequence having any number of nucleotides. More preferably, the sequence is a non-complementary sequence to the nucleotide sequence of the target nucleic acid.

The probe B is formed of a nucleotide sequence S' and a flag. The nucleotide sequence S' is complementary to a nucleotide sequence S which is a partial region of the target nucleic acid. The flag is a double strand. The double strand has an arbitrary sequence consisting of a plurality of units. The flag must not bind to the target nucleic acid and not exhibit any interaction with the target nucleic acid.

The sequences F' and S' used herein have a nucleotide of 1 or more, preferably 15 or more.

FIG. 7 shows a design of the unit. One of units of the flag FL may contain 10 bases or more, more preferably, about 15 bases. Although the flag FL has any number of units, 4 units are preferable from the view point of analysis. However, the number of units is not limited to 4.

When a plurality of target nucleic acids are simultaneously detected, the flag FL of a plurality of types of units may be used. As an example, the flag FL consists of 4 units, SD, D0, D1, ED will now be explained. This flag is formed as follows. First, 22 types of units are designed. Then, two units are selected from them as primers. One is defined as the SD unit. The other one is defined as the ED unit. Subsequently, the D0 and D1 units are selected by using the remaining 20 units. If the flag is designed by varying the combination of the two units depending upon a type of nucleic acid, 100 types of nucleic sequences can be detect (FIG. 7A).

The 22 types of units are preferably designed by orthonormal nucleotide sequences. The Tm of the orthonormal nucleotide sequences fall within almost the same range, so that they do not make a stable hybrid with the non-complementary sequences. They do not form a stable secondary structure which prevents the formation of a hybrid with the corresponding complementary sequences. Therefore, the occurrence of mis-hybridization will be reduced at the time of a final detection operation, with the result that the hybrid-formation speed can be increased. It is therefore possible to improve the detection accuracy and to reduce the detection time. Furthermore, if the number and types of units are increased, 10000 types of nucleic acid sequences can be detected.

Figure 5:
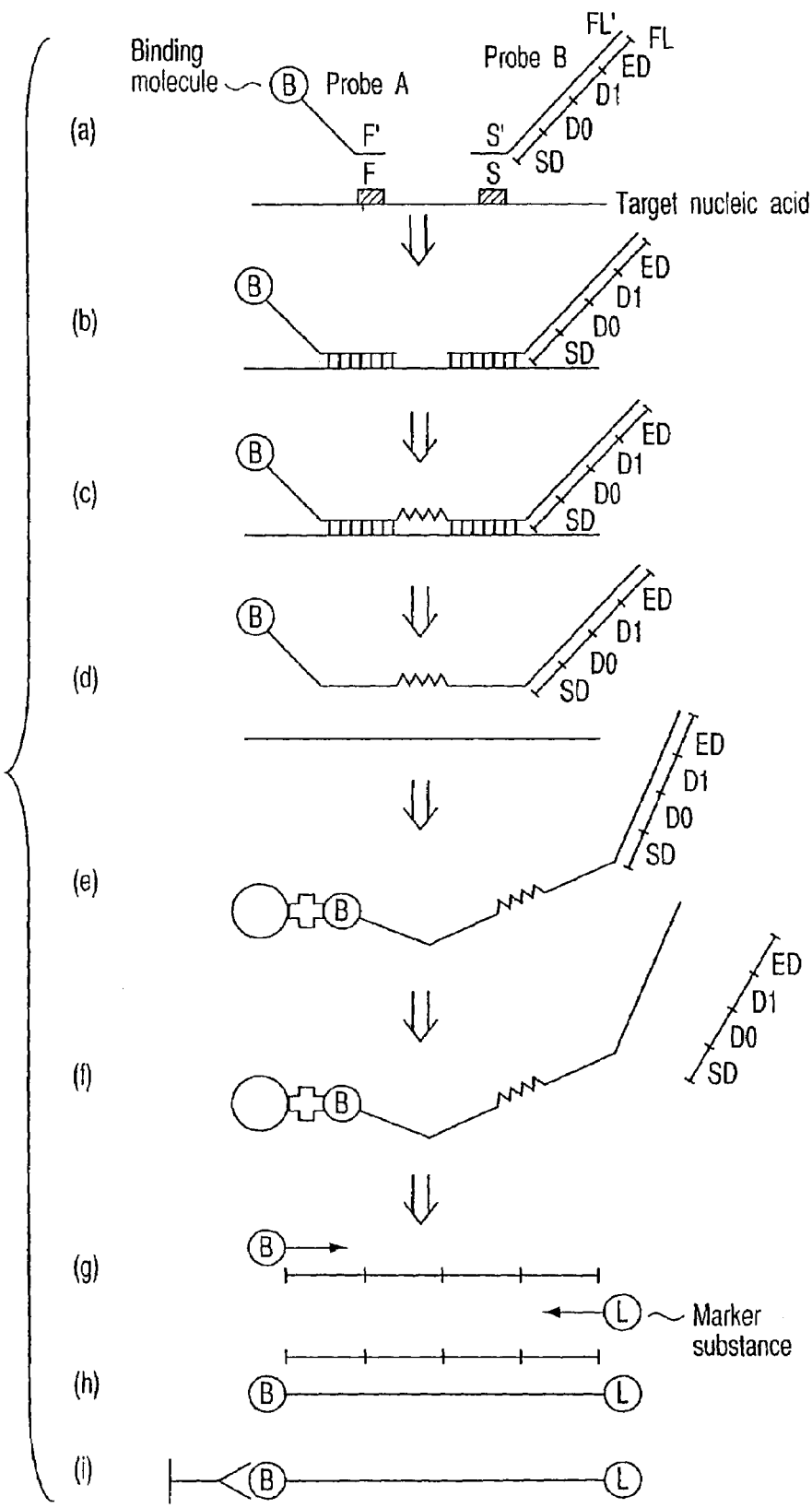
FIG. 5 is a flow chart showing Example 5 of the present invention.

Referring to FIG. 5, the method of this example will be further explained. FIG. 5a shows a flag FL consisting of 4 units, namely, SD unit, D0 unit, D1 unit, and ED unit. The SD unit serves as a primer in a polymerase chain reaction (hereinafter, referred to as a "PCR amplification" or "PCR reaction"). The D0 and D1 units are recognition units for recognizing the type of target nucleic acid. The ED unit is another primer sequence. Each of units serves as a reading frame in a later step.

Detection is performed as follows. First, the probe A and probe B are mixed with a target nucleic acid (FIG. 5a). In this case, a plurality of target nucleic acids different in sequence may be contained in a specimen. For example, if there are 100 types or less of target nucleic acids to be detected, the D0 unit is selected from 10 types of nucleic acids D0-1 to D0-10, and D1 unit is selected from 10 types of nucleic acids D1-1 o D1-10 (FIG. 7A).

Subsequently, the probe A, probe B, and target nucleic acid(s) are incubated for a predetermined time under the conditions suitable for hybridization (FIG. 5b). The hybridization conditions are the same as shown in Example 1.

Both the probes A and B hybridize with the same target nucleic acid by the hybridization thus performed (FIG. 5b).

Subsequently, the probes A and B, both being hybridized with the same nucleic acid, are ligated to each other (FIG. 5c). The conditions of ligation are the same as shown in Example 1.

The Tm value of flag FL is preferably set at a temperature higher than those of the sequences F' and S'. If the Tm value is set in this manner, it is possible to prevent denaturation of the flag, which lowers the detection sensitivity, during the heating and cooling operations at the time of hybridization, ligation, and denaturation involved in this detection method.

Subsequently, the information on the flag FL obtained is subjected to the B/F separation. More specifically, the binding molecule attached to the probe (A+B) is captured on a solid-phase carrier via a binding molecule to be paired up with the binding molecule of the probe (A+B) (FIG. 5e).

Examples of the solid phase carrier are a plate, beads, a container, a fiber, a tube, a filter, an affinity column, an electrode and the like. Preferably, beads are used.

The flag FL of the probe (A+B) bound to the binding molecule is denatured into a single strand (FIG. 5f), while keeping the binding molecule bound thereto. The resultant single-stranded sequence FL' present in a liquid phase is subjected to PCR amplification (FIG. 5g). As described, the flag FL has two primer sequences SD and ED previously arranged therein. Therefore, the PCR reaction can be easily performed by use of these primer sequences. At that time, it is preferable that a binding molecule such as biotin be bound to one of the primers for the PCR, for example, the SD sequence. The detailed PCR conditions used herein vary depending upon the flag design.

After completion of the PCR reaction, a PCR product, that is, a double-stranded sequence, is recovered by permitting the binding molecule to bind to a solid-phase carrier immobilized (FIG. 5i). The carrier immobilized is a substance capable of being paired up with the binding molecule. Further, denaturation is performed to remove the sequence FL'. Only a single-stranded sequence FL is recovered by the immobilized carrier (FIG. 5i).

Subsequently, the single-stranded flag sequence FL attached on the immobilized carrier is analyzed as follows. The immobilized carrier having the single-stranded flag sequence FL bound thereto, is equally divided into ten-portions (in this case, D1 unit consists of D1-1 to D1-10). To individual ten portions, one of D1-1' to D1-10' labeled with a marker molecule and all D0' sequences (D0-1' to D0-10') are added to hybridize them with the flag sequence FL.

Subsequently, two nucleic acid molecules thus hybridized are ligated to each other. The ligation conditions and the definitions for the marker substance are the same as previously mentioned. Thereafter, the molecule ligated is denatured and recovered in a liquid phase.

The nucleic acid molecules labeled with the marker molecule are analyzed by hybridizing them with a DNA chip or a DNA capillary on which the nucleic acid molecules of D0-1 to D0-10 are previously immobilized. Particularly, the DNA capillary is advantageous since the nucleic -acid molecules which have been divided into D0-1 to D0-10 portions, can be simultaneously analyzed. The analysis can be easily made by the DNA capillary.

As an example, the case of the flag FL which is designed by using 10 types of sequences, D0-1 to D0-10, and 10 types of sequences, D1-0 to D1-10 will now be explained. Since the sequence D0-1 is immobilized at position 1 of FIG. 7A, the nucleic acid molecule 63 ligated to a D1-1' molecule labeled with a marker molecule, is hybridized with the sequence D0-1 at position 1. Similarly, since a D0-n sequence is immobilized to a corresponding position n of the column, the nucleic acid molecule ligated to the D1' molecule (i.e., a molecule corresponding to a row) is hybridized with the position n of the column. If such a matrix arrangement is applied to the DNA capillary described later, the analysis can be readily performed (FIG. 7B).

In this example, 10 types of units are used. However, the units are not limited to 10 types. More than 10 types or less than 10 types may be used.

The "DNA capillary" used herein is a device for detecting a target nucleic acid. Since a complementary sequence to the target nucleic acid is bound inside the device, the target nucleic acid can be detected by binding the target nucleic acid to the complementary sequence. As shown in FIG. 7B, if a plurality of DNA capillaries having different probes (arranged at hatched portions) are simultaneously used, a plurality of target nucleic acids can be detected at the same time.

In the method of this example, since an orthonormal nucleotide sequence is used as each unit of the flag sequence FL, hybridization can be uniformly performed under the same conditions, e.g., a reaction temperature. Therefore, the detection can be made with a high accuracy while preventing mis-hybridization.

Furthermore, since numerous analyses can be performed simultaneously under the same conditions, the time required for the detection can be reduced.

According to the method of the present invention, complicated genomic information expressed by a nucleotide sequence of DNA can be converted into numerical values. Moreover, if calculation is made by using a DNA molecular reaction, analysis of various types of information and complicated genetic information mutually associated can be easily made. In addition, after a nucleic acid is encoded to a nucleic acid code, the nucleic acid code can be amplified easily. Therefore, even if the target sequences are present in low copy numbers, the target sequences can be accurately and quantitatively detected. Furthermore, it is possible to compress numerous data by encoding the sequence. Therefore, a number of detections can be made by using a fewer number of devices, such as a DNA chip or a capillary array.

The term "encode reaction" used herein is referred to converting a nucleotide sequence into codes based on orthonormal nucleotide sequences. The "encode reaction" includes the steps of FIGS. 5a to 5f.

The term "decode reaction" used herein is referred to reading the code converted in the above and thereby reproducing original information. The step of FIG. $5_j$ corresponds to the "decode reaction".

In Example 5, a single type of target nucleic acid is detected. If a plurality of types of flag sequences are designed, a plurality of types of target nucleic acids can be simultaneously detected by the same steps.

Figure 6:
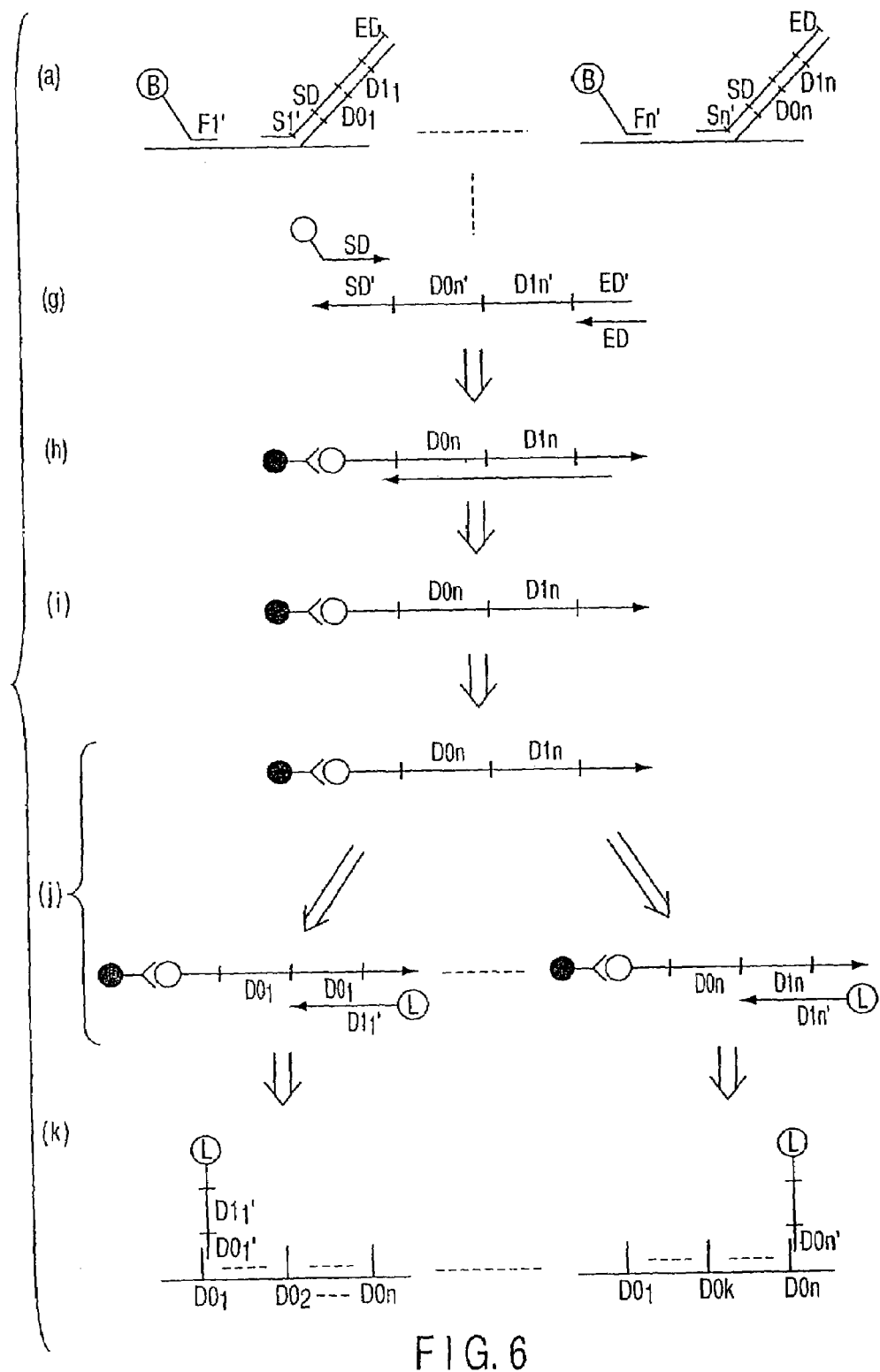
FIG. 6 is a flow chart showing a further example of the present invention.

An application example of Example 5 is shown in FIG. 6. In the example of FIG. 6, flag sequences including D01-D11 to D0n-D1n (n is an integer) are designed in accordance with the target nucleic acids to be detected. The flag sequences thus designed are treated in the same manner as in steps of FIGS. 5a to 5f and further subjected to the decode reaction described below (FIG. 6). To explain more specifically, the single-stranded sequence FL' obtained is subjected to a PCR reaction using two primer sequences SD and ED (FIG. 6g). In the steps of FIGS. 6g to 6i, a probe n is representatively shown instead of showing a plurality of probes. However, it should be interpreted that 1 to n probes are present. In this case, it is preferable that a binding molecule such as biotin should be bound to the SD sequence. The specific conditions for PCR in this case vary depending upon the design of a flag FL. The obtained double strand is recovered by using a substance capable of making a pair with the binding molecule (FIG. 6h). After the pair is denatured and washed to obtain a single strand (FIG. 6i). Subsequently, the primers complementary with respective D11-D1n sequences of each FL sequence and tagged with a marker substance, are hybridized with each FL sequence and extended (FIG. 6j).

The resultant sequences D11'-D1n' obtained are detected by using a chip or a capillary array to which the sequences D01-D1n are immobilized (FIG. 6k). The detection can be performed by the following method. A probe A is ligated to a probe B. The B/F dissociation is performed by using a binding substance attached to the probe B or using a Tgn sequence. By this method, the obtained FL can be directly detected without using PCR. In this case, the sequence to be bound to a sequence Sn' may be formed of two units. In this case, the D0n sequence and D1n sequence may be immobilized to the DNA chip or the capillary array. In this case, detection can be made by previously attaching different marker substances depending upon FL sequences. Alternatively, after the FL sequences bind to desired regions of the DNA chip, a marker substance may be attached to the FL sequences.

EXAMPLE 6

To demonstrate that the method of the present invention is useful in practice, the following experiment was performed. The sequence used herein and how to bind the sequence are shown in FIG. 8.

(1) Target Sequence and Modified Sequence

A sequence r-32-f1 was used as a target sequence (FIG. 9). A modified sequence different from the target sequence in sequence was used to confirm the specificity of the detection method. The modified sequence is designated as f1-neg-r-32AB (FIG. 9).

(2) Probe and Detection Sequence

A nucleotide b-16A was used as a probe A (FIG. 9). The symbol b of the probe A represents biotin. A nucleotide P-16B-48 was used as a probe B (FIG. 9). The probe B includes a flag FL. The symbol P represents a phosphorus group. The complementary sequence to the FL sequence of a probe B is a detection sequence, which is designated as f1-r-48 (FIG. 9).

(3) Experimental Method

The target sequence was tried to be detected by using the aforementioned probes. First, a probe B solution containing 500 pmol of probe B in a TE buffer solution of pH 8.0 was mixed with a solution for a detection sequence in an equal amount. The resultant mixture was incubated at 95° C. for one minute and decreased in temperature to 25° C. for 7 minutes. Consequently, a double-strand probe B was obtained.

The double-stranded probe B obtained, the target sequence, and the probe A were mixed. The ligation reaction was performed using a Taq DNA ligase (manufactured by New England Biolab) of 20 U in 100 μL of a ligation buffer solution. The ligation reaction was performed by gradually reducing temperature from 70° C. to 55° C. over 5 minutes to anneal the probes A, B and the target sequence. A ligation reaction was performed by adding TaqDNA ligase at 55° C. for 15 minutes. Thereafter, the temperature of the reaction is reduced to room temperature. After the ligation reaction, the specimen was added to magnetic beads on which avidin is immobilized. The resultant mixture was subjected to pre-cold wash at 30° C. to remove the target sequence unreacted. Further, cold wash was performed at the same temperature as above to remove the target sequence. After the supernatant was removed, 100 μL of TE buffer solution was added. The resultant solution was subjected to hot wash at 70° C. to recover the detection sequence.

(4) Experimental Results

Figure 10:
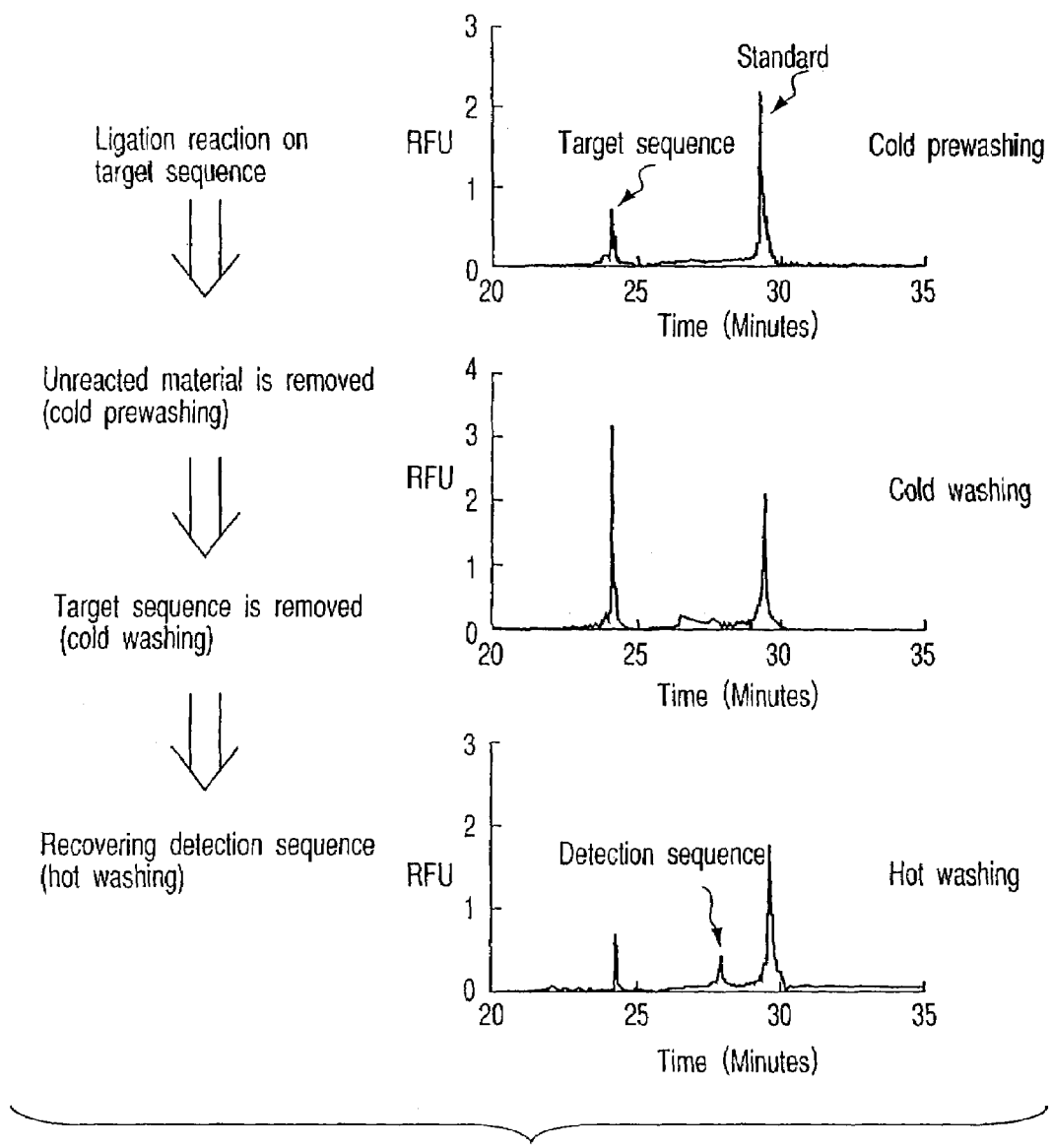
FIG. 10 is a chart showing the results of capillary electrophoresis of sequences obtained from supernatants of the individual washing processes.

The experimental results will be described below. FIG. 10 shows the results of capillary electrophoresis of the sequences obtained from the supernatants in individual washing steps. It was demonstrated that the supernatant recovered in the pre-wash contained a target sequence unused in the ligation reaction. It was also demonstrated that the supernatant recovered from the cold wash contained a target nucleotide sequence employed in the ligation reaction. It was further demonstrated that the supernatant recovered from the hot wash contained a detection sequence. More specifically, DNA having a length corresponding to the length of nucleotides of the detection sequence was detected.

Figure 11:
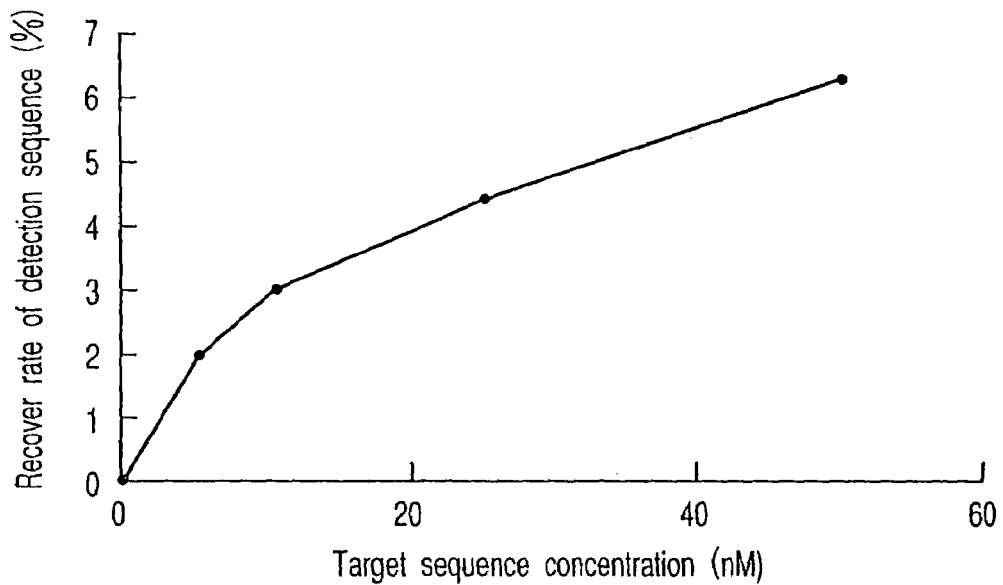
FIG. 11 is a graph showing effects of concentration of a target nucleic acid upon the recover rate of a detection nucleic acid.

FIG. 11 shows the relationship between the concentration of the target sequence and the concentration of the detection sequence recovered. More specifically, the graph of FIG. 11 shows the recovery rates (%) of the detection sequence obtained by varying the concentration of the target sequence to be added to 0, 5, 10, 20, 25 and 50 nM in the aforementioned method. As is apparent from the graph, as the concentration of the target sequence increases, the recovery rate of the detection sequence increases. This fact is one of the proofs demonstrating that the detection method of this example is useful.

Figure 12:
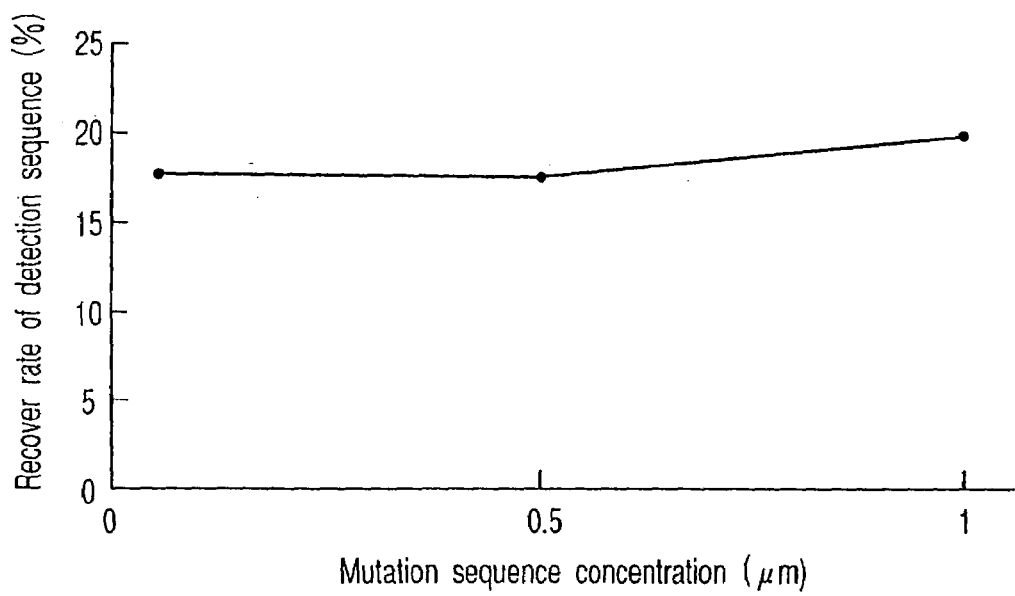
FIG. 12 is a graph showing effects of a modified sequence, which partly differs in sequence from the target sequence, upon the recover rate of the detection nucleic acid.

The specificity of the method of this example was investigated and the results are shown in FIG. 12. More specifically, the results show the recovery rate of the detection sequence when the modified sequence partially different from the target sequence in nucleotide sequence, is present in a detection system. In the aforementioned method, the modified sequence is added in amounts of 0.05, 0.5 and 1 μM simultaneously with the target sequence. As a result, the recovery rate of the detection sequence was not adversely affected by the presence of the modified sequence, as shown in FIG. 12. Therefore, it was demonstrated that the target sequence can be specifically detected by the detection method of this example.

EXAMPLE 7

Experiment

The following experiment was performed to demonstrate, in particular, the specificity and quantitative properties of the encode reaction and the decode reaction of the method of the present invention. The sequence used herein is shown in FIG. 13A. The positional relationship between individual probes and the element constituting the probes is shown in FIG. 13B.

7-1 Specificity of Encode Reaction (1) Experimental Method

First, a probe $B_{IATP}$ ($S'_{IGTP}$+SD+$D0_{IGTP}$+$D1_{IGTP}$+ED, 0.3 nM) for IGTP, a probe $B_{LRG-47}$ ($S'_{LRG-47}$+SD+$D0_{LRG-47}$+$D1_{IGTP}$+ED, 0.3 nM) for LRG-47, a probe $A_{IGTP}$ (0.3 nM) for IGTP, and an IGTP gene (0.3 nM-0.003 nM) serving as a target gene, were mixed in a ligation buffer solution, which is supplied together with Taq DNA ligase (TaqDNA ligase, manufactured by New England Biolab). The temperature of the solution mixture obtained was reduced from 70° C. at a rate of 3° C./minute. When the temperature reached 55° C., a ligase (20 units) was added to make a total volume of 30 μL. Thereafter, a ligation reaction was performed for 15 minutes, 10 mg/mL of dynabeads M-280, streptoavidin (1 μL) were added and mixed for 15 minutes. After the supernatant was removed, 20 μL of Tris EDTA buffer solution (hereinafter, simply referred to as "TE") was added. The resultant mixture was washed at 60° C. to clean probes A and B unreacted and the target nucleic acid sequence (cold wash or room-temperature wash). The washing was performed twice. After the supernatant was removed, 20 μL of TE was added. The flag sequence encoded was recovered at 95° C. Similarly, the encode reaction using LRG-47 was evaluated by ligating probes A and B responsive to the target gene LRG-47 gene. In the encode reaction, the probe ligated was subjected to PCR using the SD sequence and ED sequence as primers. Measurement was performed by capillary electrophoresis for single-strand.

(2) Experimental Results.

FIG. 15 is a scheme schematically showing steps of the experiment described above. The detection results are shown below. FIGS. 14A and 14B are the results obtained by capillary electrophoresis. As shown in FIGS. 14A and 14B, specific PCR amplification of individual FL sequences can be attained by the encode reaction of the present invention. As a result, specific PCR products are obtained.

7-2. Quantitative Properties of the PCR Amplification After the Encode Reaction (1) Experimental Method The uniformity and quantification property of the PCR performed after the encode reaction were confirmed by using the following method. The experiment was performed with respect to the flag sequences for detecting IGTP and LRG-47. The flag sequences for detecting IGTP and LRG-47 include both SD sequence and ED sequence. PCR reactions of both the flag sequences for IGTP and LRG-47 were performed by use of the SD sequence and ED sequence. The amounts of strands of both sequences added to the PCR reaction fall within 100 pM to 10 fM. The cycle of the PCR reaction consisting of 94° C./30 seconds, 65° C./30 seconds, 65° C./60 seconds, and 72° C./30 seconds, was repeated 25 times.

(2) Experimental Results

Figure 16:
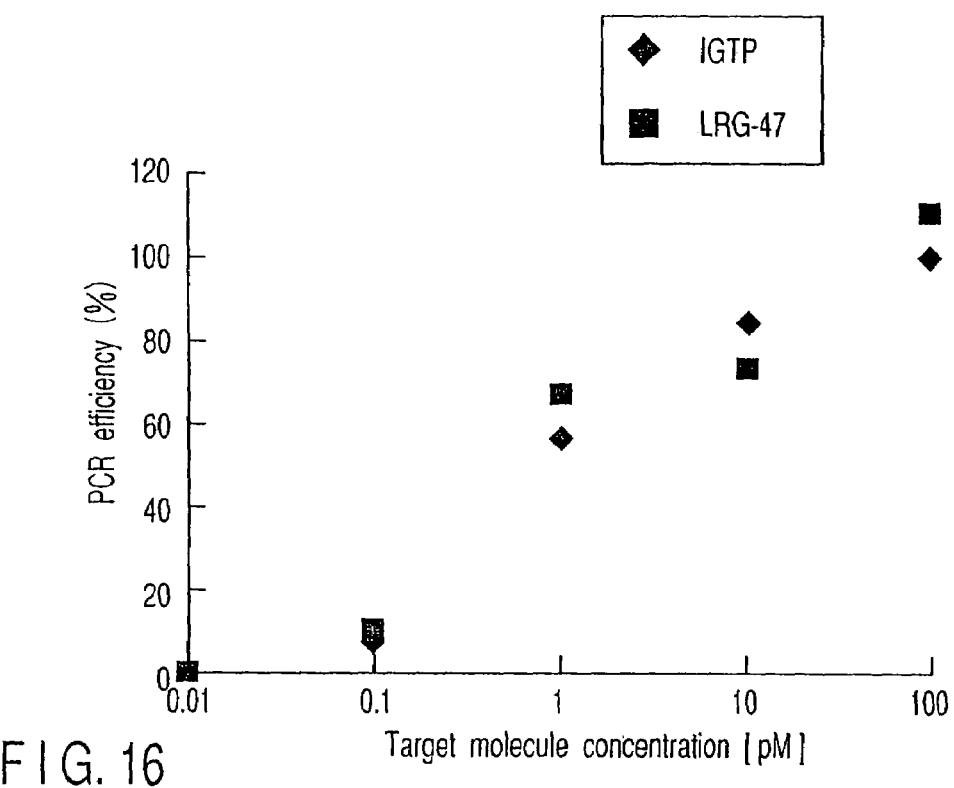
FIG. 16 is a graph showing a quantitative amplification of PCR after the encode reaction of the present invention.
Figure 17:
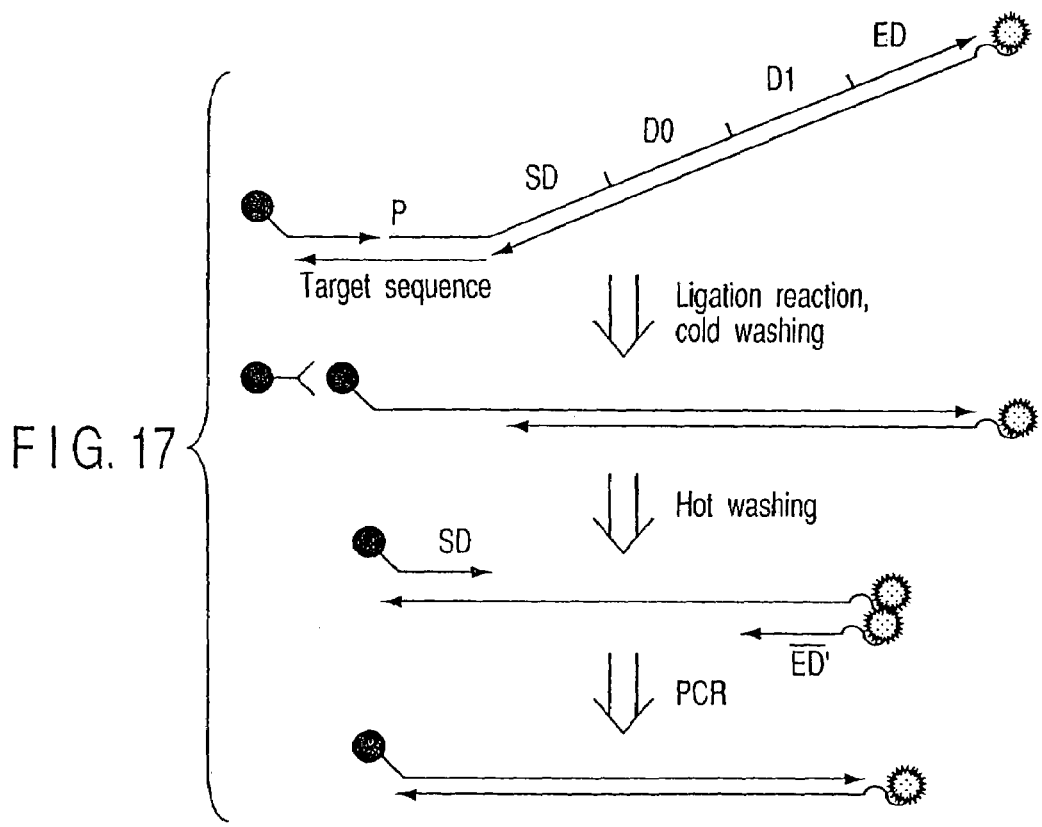
FIG. 17 is a scheme showing a method of checking quantitative amplification of PCR after the encode reaction of the present invention.

FIG. 17 is a scheme schematically showing steps of the experiment mentioned above. The detection results are shown below. FIG. 14 are the results obtained by capillary electrophoresis. As shown in FIG. 16, the amount of PCR amplification after the encode reaction of the present invention varies depending upon the concentration of the target sequence.

7-3. Specificity and Quantitative Properties of the Decode Reaction (1) Experimental Method The sequences used herein are the same as mentioned above. More specifically, an SD+$D0_{IGTP}$+$D1_{IGTP}$+ED sequence added with biotin (hereinafter, also referred to as "b-code 1") and SD+$D0_{LRG-47}$+$D1_{LRG-47}$+ED (hereinafter, also referred to as "b-code 2") were subjected to a decode reaction. 0.2 µL of the b-code 1 and b-code 2 (concentration: 100 µM) were mixed with a TE buffer (49.8 µL) containing 1M NaCl and 40 µL of dynabeads M-280 streptoavidin (10 mg/mL). The resultant solution was stirred for 15 minutes, washed, at room temperature, and then, the supernatant was removed. To the obtained beads, a TE buffer solution of 50 µL was added, and the mixture was washed at room temperature. After the supernatant was removed, a further 50 µL of TE buffer solution was added to the beads obtained. The resultant beads were washed at 80° C. and the supernatant was removed. Thereafter, the resultant beads was washed at room temperature with a ligation buffer and the supernatant was removed. Subsequently, a reverse strand relative to D1 and reverse strands relative to $D0_{IGTP}$ and $D0_{LRG-47}$ were added to the resultant beads to a final concentration of 400 nm, individually. The temperature of the resultant mixtures was raised to 95° C. to convert the reverse strand into a single-strand reverse strand. The temperature was further reduced at a rate of 7° C. per minute. Subsequently, Taq ligase of 20 units were added at 60° C. to the resultant mixture, the ligation reaction was performed for 15 minutes. After the supernatant was removed, 50 µL of the TE buffer was added to the reaction solution. The resultant mixture was washed at room temperature. Thereafter, the supernatant was removed, 50 µL of the TE buffer was again added. The temperature of the reaction solution was increased to 80° C. and the supernatant was recovered. In this manner, the probes ligated was recovered. The streptoavidin beads (40 µL) were added to the supernatant obtained and further a TE buffer solution (12.5 µL) containing 1M NaCl was added, and stirred for 15 minutes. Thereafter, the supernatant was recovered at 80° C., an aliquot (20 µL) of the supernatant was added to each of two tubes. The probe (b-1) having the sequence corresponding to $D0_{IGTP}$ having biotin added thereto and the probe (b-2) having the sequence corresponding to $D0_{LRG-47}$ having biotin added thereto were added to each of two tubes in an amount of 100 µmol. To the resultant solution, further 16 µL of TE buffer solution containing 2M NaCl was added. The resultant mixture was increased to a temperature to 95° C. Thereafter, the temperature of the mixture was reduced to 25° C. at a rate of 10° C. per minute. In this manner, hybridization was performed. To this solution, 40 µL of the streptoavidin was added and the solution mixture was stirred for 15 minutes. Thereafter, the supernatant was removed and 40 µL of TE buffer solution was added to the resultant mixture. The mixture was washed at 40° C. Subsequently, the supernatant-was removed and the TE buffer solution (40 µL) was further added, and the temperature of the resultant mixture was increased to 70° C. The supernatant was recovered, and each supernatant was subjected to capillary electrophoresis for a single strand.

(2) The Experimental Results

FIG. 19 is a scheme schematically the steps of the experiment described above. The detection results are shown below. FIGS. 18A and 18B are the results obtained by capillary electrophoresis. The decode of the present invention was performed by ligating a PCR product amplified by the encode reaction with D0 and labeled D1 sequences corresponding to respective genes. The probes ligated were detected by $D1_{IGTP}$ and $D1_{LRG-47}$ labeled with biotin. As a result, it was demonstrated that the product corresponding to each of genes can be specifically detected, as shown in FIG. 17.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of simultaneously detecting or quantifying n kinds of different target nucleic acids in a specimen, wherein each of the n kinds of different target nucleic acids contains a first partial sequence Fa and a second partial sequence Sa and is set forth as Fa-Sa, wherein said Fa is one of sequences F1 to Fn, and said Sa is one of sequences S1 to Sn, wherein n is an integer of 2 or more comprising:
   (a) preparing different nucleic acid probes A1 to An and different nucleic acid probes B1 to Bn, Aa is one of the nucleic acid probes A1 to An and Ba is one of the nucleic acid probes B1 to Bn, wherein n is an integer of 2 or more,
      said probe Aa has a sequence F'a complementary to the first partial sequence Fa of the target nucleic acid Fa Sa and a first binding molecule bound to the sequence F'a, wherein said F'a is one of sequences F'1 to F'n and the first binding molecule is a part of said probe Aa, and wherein n is an integer of 2 or more, and
      said probe Ba has a sequence S'a complementary to the second partial sequence Sa of the target nucleic acid and a sequence hybridized with a flag sequence, wherein said flag sequence is a part of said probe Ba and comprises four nucleic acid sequences SD, $D0_j$, $D1_k$, and ED, each of said SD, $D0_j$, $D1_k$, and ED having a desired sequence, and linked in the form of SD-$D0_j$-$D1_k$-ED; wherein the sequences $D0_j$ and $D1_k$ are located between said SD and ED and a sequence combination of $D0_j$ and $D1_k$ is set forth as $D0_j$-$D1_k$; and wherein said SD and ED are primer sequences, wherein said S'a is one of sequences S'1 to S'n, said $D0_j$ is one of sequences $D0_1$ to $D0_n$, and said $D1_k$ is one of sequences $D1_1$ to $D1_n$, and wherein n is an integer of 2 or more and said $D0_j$-$D1_k$ in said flag sequence of each of the nucleic acid probes B1 to Bn are different,
   (b) mixing said probes A1 to An and said probes B1 to Bn with the specimen, respectively, thereby hybridizing said probes A1 to An with their corresponding said F1 to Fn of the n kinds of different target nucleic acids and simultaneously hybridizing said probes B1 to Bn with their corresponding said S1 to Sn of the n kinds of different target nucleic acids;
   (c) ligating said probes A1 to An that are located on said F1 to Fn of the n kinds of different target nucleic acids to their corresponding said probes B1 to Bn that are located on said S1 to Sn of the n kinds of different target nucleic acids, thereby obtaining n kinds of different ligated probes A1-B1 to An-Bn wherein each said ligated probes A1-B1 to An-Bn comprises one said flag sequence;
   (d) binding the first binding molecule of said probes A1 to An in said ligated probes A1-B1 to An-Bn to substances capable of being paired with the first binding molecule, thereby dissociating said ligated probes A1-B1 to An-Bn from the n kinds of different target nucleic acids;
   (e) obtaining n kinds of different flag sequences by isolating each said flag sequence from said ligated probes A1-B1 to An-Bn;
   (f) amplifying the n kinds of different flag sequences by polymerase chain reaction (PCR), wherein the PCR uses a primer labeled with a marker substance and the n kinds of different flag sequences as templates, and thereby obtaining n kinds of different amplification products labeled with the marker substance; and
   (g) detecting or quantifying the n kinds of different amplification products labeled with the marker substance, and thereby detecting or quantifying the n kinds of different target nucleic acids in the specimen.

2. The method according to claim 1, wherein step (f) further comprises:
   another primer labeled with a second binding molecule, and thereby obtains n kinds of different amplification products labeled with the marker substance and the second binding molecule, and binding the second binding molecules of the n kinds of different amplification products labeled with the marker substance and the second binding molecule to substances capable of being paired with the second binding molecule, thereby recovering the n kinds of different amplification products labeled with the marker substance and the second binding molecule.

3. The method according to claim 1, wherein, in said step (d), said substances capable of being paired with the first binding molecules are immobilized on beads such that said ligated probes A1-B1 to An-Bn are dissociated from the n kinds of different target nucleic acids by binding said ligated probes A1-B1 to An-Bn to the beads via the first binding molecules.

4. The method according to claim 1, wherein said marker substance is a fluorescent substance.

* * * * *